(12) United States Patent
Alabugin et al.

(10) Patent No.: US 8,410,303 B2
(45) Date of Patent: Apr. 2, 2013

(54) DIRECT CONVERSION OF PHENOLS INTO AMIDES AND ESTERS OF BENZOIC ACID

(75) Inventors: Igor Alabugin, Tallahassee, FL (US); Abdulkader Baroudi, Paris (FR)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 160 days.

(21) Appl. No.: 13/053,756

(22) Filed: Mar. 22, 2011

(65) Prior Publication Data
US 2011/0237798 A1  Sep. 29, 2011

Related U.S. Application Data

(60) Provisional application No. 61/316,704, filed on Mar. 23, 2010.

(51) Int. Cl.
*C07C 69/84* (2006.01)
*C07C 233/65* (2006.01)

(52) U.S. Cl. .................................. 560/109; 564/184

(58) Field of Classification Search ................. None
See application file for complete search history.

(56) References Cited

PUBLICATIONS

Falvey et al, Journal of Physical Chemistry, Neophyl-like Rearrangement of Alkoxy Radicals: Direct Detection of a Bridged Intermediate by Time-Resolved Absorption Spectroscopy, 1990, 94, pp. 1056-1059.*

Christopher F. J. Barnard, Palladium-Catalyzed Carbonylation—A Reaction Come of Age, Organometallics, 2008, 5402-5422, vol. 27, American Chemical Society.

Anne Brennfuhrer, et al., Palladium-Catalyzed Carbonylation Reactions of Aryl Halides and Related Compounds, Palladium Catalysis, Angewandte Chemie, Int. Ed., 2009, 4114-4133, vol. 48, Wiley-VCH Verlag GmbH & Co. KGaA, Weinheim.

Rongloiang Lou, et al, Preparation of N-hydroxysuccinimido esters via palladium-catalyzed carbonylation of aryl triflates and halides, Science Direct, Tetrahederon Letters, 2003, 2477-2480, vol. 44, Elsevier Science Ltd.

Obaidur Rahman, et al., Aryl Triflates and [11C]/(13C)Carbon Monoxide in the Synthesis of 11C-/13C-Amides, JOC Article, 2003, 3558-3562, vol. 68, American Chemical Society.

Obaidur Rahman, et al., Synthesis of N-methyl-N-(1-methylproply)-1-(2-chlorophenyl)-isoquinoline-3-[11C] carboxamide ([11C-carbonyl]PK11195) and some analogues using [11C]carbon monoxide and 1-(2-chlorophenyl) isoquinolin-3-yl triflate, J. Chem, So., Perkin Trans. 2002, 2699-2703, vol. 1, The Royal Society of Chemistry.

* cited by examiner

*Primary Examiner* — Paul A Zucker
(74) *Attorney, Agent, or Firm* — Armstrong Teasdale LLP

(57) ABSTRACT

A method is provided for the preparation of an aromatic carboxylic acid aryl ester or an N-aryl aromatic carboxamide. The method comprises contacting an O,O-diaryl thiocarbonate or an O-aryl-N-aryl thiocarbamate with a reactant that regioselectively reacts with sulfur, which contact causes an O-neophyl rearrangement, thereby forming either the aromatic carboxylic acid aryl ester or the N-aryl aromatic carboxamide, respectively.

16 Claims, No Drawings

DIRECT CONVERSION OF PHENOLS INTO AMIDES AND ESTERS OF BENZOIC ACID

CROSS REFERENCE TO RELATED APPLICATIONS

This application claims priority from U.S. Provisional Application Ser. No. 61/316,704, filed on Mar. 23, 2010, the disclosure of which is incorporated herein as if set forth in its entirety.

STATEMENT REGARDING FEDERALLY SPONSORED RESEARCH

This invention was made with government support under Grant No. CHE-0848686 awarded by the National Science Foundation. The government has certain rights in the invention.

FIELD OF THE INVENTION

The present invention generally relates to a method that achieves transformation between organic functional groups, in particular conversion of aromatic alcohols into aromatic carboxylic acid aryl esters and N-aryl-aromatic carboxamides. More specifically, the present invention relates to a method effecting the transformation of a phenol into a benzoic acid derivative, such as a benzoic acid aryl ester or an N-aryl-benzamide.

BACKGROUND OF THE INVENTION

Direct transformations between functional groups simplify the chemical landscape and allow more efficient execution of multistep synthetic routes. While phenols and benzoic acid derivatives are among the most common organic functionalities, the ways for transforming a phenol into an aryl carboxylic acid derivative, such as esters and amides of benzoic acid, are still limited.

Palladium-catalyzed carbonylation of aromatic triflates is a commonly used transformation known in the literature. See, for example, Barnard, C. F. J. *Organometallics* 2008, 27, 5402; Brennfuhrer, A.; Neumann, H.; Beller, M. *Angew. Chem., Int. Ed.* 2009, 48, 4114; Lou, R.; VanAlstine, M.; Sun, X.; Wentland, M. P. *Tetrahedron Lett.* 2003, 44, 2477; Rahman, O.; Kihlberg, T.; Långström, B. *J. Org. Chem.* 2003, 68, 3558; Rahman, O.; Kihlberg, T.; Långström, B. *J. Chem. Soc. Perkin Trans.* 1 2002, 2699; Gerlach, U.; Wollmann, T. *Tetrahedron Lett.* 1992, 33, 5499; Cacchi, S.; Lupi, A. *Tetrahedron Lett.* 1992, 33, 3939; Dolle, R. E.; Schmidt, S. J.; Kruse, L. I. *J. Chem. Soc. Chem. Commun.* 1987, 904; and Cacchi, S.; Ciattini, P. G.; Morera, E.; Ortar, G. *Tetrahedron Lett.* 1986, 27, 3931. The method suffers from the disadvantage that palladium is classified as a Class I metal (significant safety concern) in pharmaceuticals with permitted daily exposure of less 10 μg/day. See Committee for Human Medicinal Products (CHMP): Guideline on the Specification Limits for Residues of Metal Catalysts or Metal Reagents (Doc. Ref. CPMP/SWP/QWP/4446/2000).

SUMMARY OF THE INVENTION

Among the aspects of the present invention may be noted a reaction sequence that brings about conversion between an aromatic alcohol (e.g., a phenol) into a aromatic carboxylic acid derivative, such as an aromatic carboxylic acid aryl esters (e.g., a benzoic acid aryl ester such as phenyl benzoate) or an N-aryl-aromatic carboxamide (e.g., an N-aryl-benzamide such as N-phenylbenzamide). The method can be applied to aromatic alcohols comprising fused rings (e.g., naphthalen-1-ol, naphthanlen-2-ol, anthracenols, phenanthrenols, and others) to prepare aromatic carboxylate aryl esters comprising fused rings such as a naphthoic acid aryl ester, an anthracene carboxylic acid aryl ester, a phenanthrene carboxylic acid aryl ester, and the like (e.g., phenyl 1-naphthoate, phenyl 2-naphthoate, or phenyl-9-phenanthroate) or N-aryl aromatic carboxamides comprising fused rings such as an N-aryl naphthamide, an N-aryl phenanthrene carboxamide, an N-aryl anthracene carboxamide, and the like (e.g., N-phenyl-1-naphthamide, N-phenyl-2-naphthamide, N-phenylphenanthrene-1-carboxamide).

Briefly, therefore, the invention is directed to a method for the preparation of an aromatic carboxylic acid aryl ester. The method comprises contacting an O,O-diaryl thiocarbonate with a reactant that regioselectively reacts with sulfur, which contact causes an O-neophyl rearrangement, thereby forming the aromatic carboxylic acid aryl ester.

The invention is further directed to a method for the preparation of an N-aryl aromatic carboxamide. The method comprises contacting an O-aryl-N-aryl thiocarbamate with a reactant that regioselectively reacts with sulfur, which contact causes an O-neophyl rearrangement, thereby forming the N-aryl aromatic carboxamide.

Other objects and features will be in part apparent and in part pointed out hereinafter.

DETAILED DESCRIPTION OF THE EMBODIMENT(S) OF THE INVENTION

The present invention is directed to a method of converting an aromatic alcohol into an aromatic carboxylic acid derivative, such as an aromatic carboxylic aryl ester or an N-aryl aromatic carboxamide. This transformation can be applied in organic synthesis and modification of any chemical which comprises an aromatic alcohol moiety (drugs, biomolecules, natural and synthetic products).

For example, in some embodiments, the method of the present invention may be used to convert a phenol (substituted or unsubstituted) into a benzoic acid derivative, specifically a benzoate ester or a benzamide. More specifically, in some embodiments, the method of the present invention may be used to convert a substituted or unsubstituted phenol into a benzoic acid aryl ester (e.g., phenyl benzoate) or an N-aryl benzamide (e.g., N-phenylbenzamide).

The method of the present invention may be used to convert aromatic alcohols comprising two or more fused rings such as naphthenols, anthracenols, phenanthrenols, phenalenols, pyrenols, benz(a)anthracenols, benzo[c]phenanthrenols, tetracenols, chrysenols, triphenylenols, etc. into aromatic carboxylic acid aryl esters and N-aryl aromatic carboxamides. In some embodiments, the method may be applied to aromatic alcohols comprising fused rings (e.g., naphthalen-1-ol, naphthalen-2-ol, phenanthrenols, anthracenols, etc.) to prepare aromatic carboxylic acid aryl esters comprising fused rings such as a naphthoic acid aryl ester, an anthracene carboxylic acid aryl ester, a phenanthrene carboxylic acid aryl ester, and the like (e.g., phenyl 1-naphthoate, phenyl 2-naphthoate, phenyl or phenyl-9-phenanthroate). In some embodiments, the method may be applied to aromatic alcohols comprising fused rings (e.g., naphthalen-1-ol, naphthalen-2-ol, phenanthrenols, anthracenols, etc.) to prepare N-aryl aromatic carboxamides comprising fused rings such as an N-aryl naphthamide, an N-aryl phenanthrene carboxamide, an N-aryl anthracene carboxamide, and the like (e.g., N-phenyl-1-naphthamide, N-phenyl-2-naphthamide, N-phenylphenanthrene-1-carboxamide).

The method of the present invention employs a radical cascade that dramatically increases the overall efficiency of the conversion compared to methods known in the art. Among the considerations in providing an efficient reaction sequence for converting an aromatic alcohol into an aromatic carboxylic acid aryl esters or an N-aryl aromatic carboxamide (e.g., a benzoic acid aryl ester or an N-aryl benzamide), the reaction process of the present invention begins with a functional group which is readily prepared from aromatic alcohols, e.g., phenols. The design incorporates an efficient step which selectively creates a radical at the correct carbon atom from the functional group in either an intra- or intermolecular manner. This radical is sufficiently reactive such that the radical undergoes a C—O transposition through the ipso-attack at the aromatic ring followed by the C—O bond cleavage. In other words, substituents X and Z as shown in the following reaction Scheme (1) do not deactivate the radical center through either excessive stabilization of the latter or through β-scission step. Finally, the transposed radical possesses a weak C—X bond which can undergo an efficient β-scission step which renders the overall process irreversible and completes the cascade. The requirements of this reaction sequence, as outlined above, are depicted in the following reaction Scheme (1):

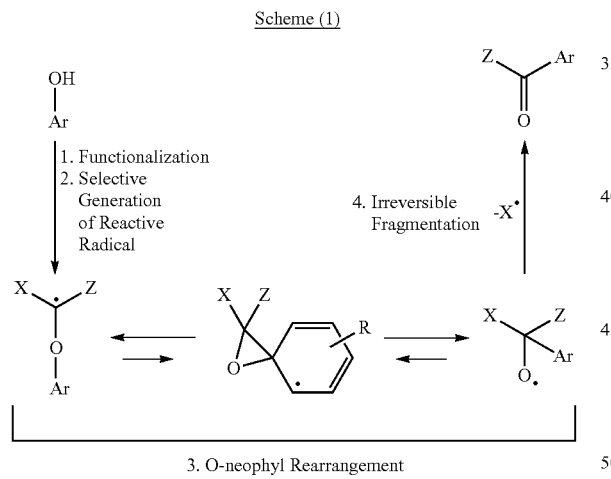

Scheme (1)

3. O-neophyl Rearrangement

This invention provides a new and efficient procedure for the transformations of an aromatic alcohol (e.g., a phenol) into an aromatic carboxylic acid aryl ester or an N-aryl aromatic carboxamide (e.g., a benzoic acid aryl ester or an N-aryl benzamide) through just such a radical cascade. This process offers a novel and straightforward method for making carbon-carbon bonds via a radical transposition of oxygen and carbon atoms. The method generally comprises the steps of converting an aromatic alcohol into a thiocarbonate (e.g., an O,O-diaryl thiocarbonate) or thiocarbamate (e.g., an O-aryl-N-aryl thiocarbamate), and then subjecting the thiocarbonate or thiocarbamate to a radical rearrangement in the presence of a radical agent. The relatively high yields for the formation of the rearranged products (up to 98%) render this reaction a very promising new tool in the organic synthesis of complex molecules. Using this radical transformation, chemists would not only be able to find easier routes for making organic molecules from inexpensive commercially available phenols, but also modify existing drugs and natural products that are phenol derivatives.

An overall reaction sequence for the conversion of an aromatic alcohol, such as a phenol, in the preparation of either a aromatic carboxylic acid aryl ester (e.g., a benzoic acid aryl ester) or an N-aryl aromatic carboxamide (e.g., an N-aryl benzamide) is depicted below as Scheme (2):

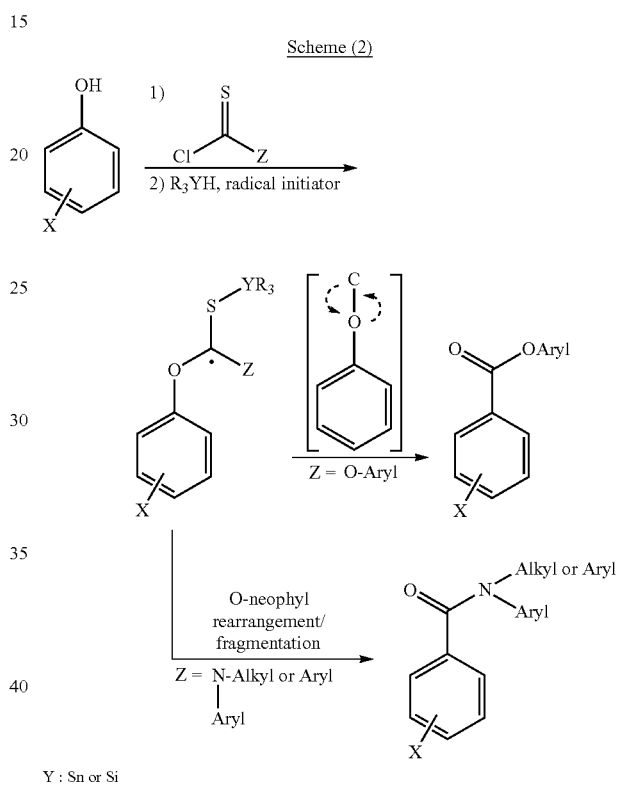

Scheme (2) depicts the formation of an O,O-diaryl thiocarbonate (top sequence) or an O-aryl-N-aryl thiocarbamate (bottom sequence) via reaction with a thiocarbonyl compound having a leaving group (in this example, chloride). The thiocarbonate or thiocarbamate undergoes O-neophyl rearrangement via reaction with a Sn- or Si-centered radical initiator, thereby yielding the product aromatic carboxylic acid aryl ester or an N-aryl aromatic carboxamide. As will be shown in the examples, the rearrangement occurs at high yield.

I. Conversion of Aromatic Alcohol into Aromatic Carboxylic Acid Aryl Ester

In some embodiments, the process of the present invention is directed to a method for converting an aromatic alcohol into an aromatic carboxylic acid aryl esters (e.g., a benzoic acid aryl ester, a naphthoic acid aryl ester, etc.). The aromatic carboxylic acid aryl ester may have the following general Structure (I):

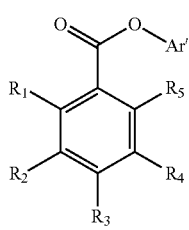

Structure (I)

wherein $R_1$, $R_2$, $R_3$, $R_4$, and $R_5$ are each independently a hydrogen, an alkyl, an alkenyl, an alkynyl, an alkoxy, a cyano, an aryl, an aromatic heterocycle, an ester, an amino, a hydrazide, an amide, thioether, sulfone, sulfoxide, sulfonic esters, and sulfinic esters, a carboxylate, or a halide. The various moieties that make up $R_1$, $R_2$, $R_3$, $R_4$, and $R_5$ may be substituted or unsubstituted and generally comprise from 0 to about 24 carbon atoms, from one to about 24 carbon atoms, such as from about 1 to about 12 carbon atoms, or from about 1 to about 6 carbon atoms. Exemplary moieties that may contain no carbon include, for example, sulfone, sulfoxide, sulfonic esters, and sulfinic esters, amino, hydrazide, or halides bonded directly to the aromatic ring. Certain of these moieties, e.g., amino, may optionally be substituted with carbon-containing groups, commonly alkyl having from 1 to 12 carbon atoms. The halide may be fluoride, chloride, bromide, or iodide. Exemplary substituents containing one carbon atom include, for example, cyano, methyl, methoxy, and methylamino. Exemplary substituents containing two carbon atoms include, for example, ethyl, ethoxy, ethylamino, dimethylamino, and methylcarboxylate. Exemplary substituents containing three carbon atoms include, for example, n-propyl, isopropyl, n-propoxy, isopropoxy, methylethylamino, and ethylcarboxylate.

Experimental results to date indicate that the O-neophyl reaction is accelerated by substituents which have either a lone pair (e.g., alkoxy (OR) and amino (NRR')) or a π-bond (e.g., cyano (CN)) at the ortho or para position, independent of whether these substituents are donors or acceptors. It has also been observed that substituents at the meta position have very little effect.

In some embodiments, any $R_1$, $R_2$, $R_3$, $R_4$, and $R_5$ together with an adjacent R group (e.g., $R_1$ and $R_2$, or $R_2$ and $R_3$), the atoms to which they are bonded in the aryl group, and additional atoms (not shown) form a cyclic moiety, such as a fused aromatic ring. Exemplary aromatic rings comprising fused ring structures include naphthalene, anthracene, phenanthrene, pyrene, benz(a)anthracene, benzo[c]phenanthrene, tetracene, chrysene, and triphenylene. The fused ring structures may be heteroaromatic comprising nitrogen, oxygen, or sulfur atoms, and the fused ring may be an aromatic heterocyclic ring, such as quinoline, isoquinoline, pyridine, quinoxaline, quinazoline, cinnoline, pyrimidine, acridine, and the like.

In some embodiments, any $R_1$, $R_2$, $R_3$, $R_4$, and $R_5$ may comprise a cyclic structure that is not fused to the ring, for example, a phenyl, a pyridyl, etc.

In the above Structure (I), Ar' denotes an aromatic ring containing moiety, which may be the same or different as the ring depicted in Structure (I) as having substituents $R_1$ through $R_5$.

A. Preparation of Thiocarbonate from Aromatic Alcohol

In the first step of the reaction sequence for the preparation of an aromatic carboxylic acid aryl ester (e.g., a benzoic acid aryl ester, a naphthoic acid aryl ester, etc.) having Structure (I), an aromatic alcohol is reacted with a compound containing thiocarbonyl (C=S) moiety in order to prepare a thiocarbonate. The thiocarbonate contains a pair of aryloxy moieties bonded to the thiocarbonyl (C=S) moiety such that the thiocarbonate comprises an O,O-diaryl thiocarbonate and has a general structure:

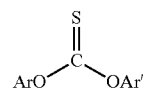

wherein Ar and Ar' are aryl moieties, which aryl moieties may be the same or different.

An aromatic alcohol for reacting with the thiocarbonyl-containing compound may have the following Structure (II):

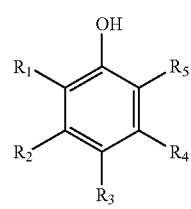

Structure (II)

wherein $R_1$, $R_2$, $R_3$, $R_4$, and $R_5$ are each independently a hydrogen, an alkyl, an alkenyl, an alkynyl, an alkoxy, a cyano, an aryl, an aromatic heterocycle, an ester, an amino, a hydrazide, an amide, thioether, sulfone, sulfoxide, sulfonic esters, and sulfinic esters, a carboxylate, or a halide. The various moieties that make up $R_1$, $R_2$, $R_3$, $R_4$, and $R_5$ may be substituted or unsubstituted and generally comprise from 0 to about 24 carbon atoms, from one to about 24 carbon atoms, such as from about 1 to about 12 carbon atoms, or from about 1 to about 6 carbon atoms. Exemplary moieties that may contain no carbon include, for example, sulfone, sulfoxide, sulfonic esters, and sulfinic esters, amino, hydrazide, or halides bonded directly to the aromatic ring. Certain of these moieties, e.g., amino, may optionally be substituted with carbon-containing groups, commonly alkyl having from 1 to 12 carbon atoms. The halide may be fluoride, chloride, bromide, or iodide. Exemplary substituents containing one carbon atom include, for example, cyano, methyl, methoxy, and methylamino. Exemplary substituents containing two carbon atoms include, for example, ethyl, ethoxy, ethylamino, dimethylamino, and methylcarboxylate. Exemplary substituents containing three carbon atoms include, for example, n-propyl, isopropyl, n-propoxy, isopropoxy, methylethylamino, and ethylcarboxylate.

Experimental results to date indicate that the O-neophyl reaction is accelerated by substituents which have either a lone pair (e.g., alkoxy (OR) and amino (NRR')) or a π-bond (e.g., cyano (CN)) at the ortho or para position, independent of whether these substituents are donors or acceptors. It has also been observed that substituents at the meta position have very little effect.

In some embodiments, any $R_1$, $R_2$, $R_3$, $R_4$, and $R_5$ together with an adjacent R group (e.g., $R_1$ and $R_2$, or $R_2$ and $R_3$), the atoms to which they are bonded in the aryl group, and additional atoms (not shown) form a cyclic moiety, such as a fused aromatic ring. Exemplary aromatic rings comprising fused ring structures include naphthalene, anthracene, phenanthrene, pyrene, benz(a)anthracene, benzo[c]phenanthrene, tetracene, chrysene, and triphenylene. The additional atoms may comprise nitrogen or oxygen, and the fused ring may be a aromatic heterocyclic ring, such as quinoline, isoquinoline, pyridine, quinoxaline, quinazoline, cinnoline, pyrimidine, acridine, etc.

In some embodiments, any $R_1$, $R_2$, $R_3$, $R_4$, and $R_5$ may comprise a cyclic structure that is not fused to the ring, for example, a phenyl, a pyridyl, etc.

In some preferred embodiments, the aromatic alcohol comprises a substituted or unsubstituted phenol. In some embodiments, the aromatic alcohol comprises two fused aromatic rings, such that the aromatic alcohol comprises a substituted or unsubstituted naphthane-1-ol or a substituted or unsubstituted naphthane-2-ol. In some embodiments, the aromatic alcohol comprises more than two fused rings, such as three, four, or more, such that the aromatic alcohols comprises a substituted or unsubstituted anthracenol such as anthracen-1-ol, anthracen-2-ol, anthracen-9-ol, a substituted or unsubstituted phenathrenol such as phenanthren-1-ol, phenanthren-2-ol, phenanthren-3-ol, phenanthren-4-ol, phenanthren-9-ol, a substituted or unsubstituted phenalenol, a substituted or unsubstituted pyrenol, a substituted or unsubstituted benz(a)anthracenol, a substituted or unsubstituted benzo[c]phenanthrenol, a substituted or unsubstituted tetracenol, a substituted or unsubstituted chrysenol, a substituted or unsubstituted triphenylenol, and the like.

In some embodiments, each of $R_1$, $R_2$, $R_3$, $R_4$, and $R_5$ is hydrogen, and the aromatic alcohol is phenol. In some embodiments, any $R_1$, $R_2$, $R_3$, $R_4$, and $R_5$ together with an adjacent R group and the atoms to which they are bonded form a cyclic moiety, such as a 6-membered ring fused to the ring having substituents $R_1$, $R_2$, $R_3$, $R_4$, and $R_5$, i.e., naphthane-1-ol or naphthane-2-ol. In some embodiments, each of $R_3$, $R_4$, and $R_5$ are hydrogen, and $R_1$ and $R_2$, together with the carbons to which they are bonded form a 6-membered ring fused to the phenol ring, i.e., naphthane-1-ol. In some embodiments, each of $R_1$, $R_4$, and $R_5$ are hydrogen, and $R_2$ and $R_3$, together with the carbons to which they are bonded form a 6-membered ring fused to the phenol ring, i.e., naphthane-2-ol. In some embodiments, each of $R_1$, $R_2$, $R_4$, and $R_5$ are hydrogen, and $R_3$ is an alkoxy moiety, preferably a methoxy, ethoxy, n-propoxy, or isopropoxy. In some preferred embodiments, the alkoxy is a methoxy, i.e., the structure is 4-methoxyphenol. In some embodiments, each of $R_1$, $R_2$, $R_4$, and $R_5$ are hydrogen, and $R_3$ is a cyano, i.e., the structure is 4-hydroxybenzonitrile. In some embodiments, each of $R_1$, $R_2$, $R_4$, and $R_5$ are hydrogen, and $R_3$ is a chloride, i.e., the structure is 4-chlorophenol. In some embodiments, each of $R_1$, $R_2$, $R_4$, and $R_5$ are hydrogen, and $R_3$ is a bromide, i.e., the structure is 4-bromophenol. In some embodiments, each of $R_1$, $R_2$, $R_4$, and $R_5$ are hydrogen, and $R_3$ is a fluoride, i.e., the structure is 4-fluorophenol. In some embodiments, each of $R_1$, $R_2$, $R_4$, and $R_5$ are hydrogen, and $R_3$ is methyl, i.e., the structure is p-cresol. In some embodiments, each of $R_1$, $R_2$, $R_4$, and $R_5$ are hydrogen, and $R_3$ is phenyl, i.e., the structure is [1,1'-biphenyl]-4-ol. In some embodiments, each of $R_1$, $R_2$, $R_4$, and $R_5$ are hydrogen, and $R_3$ is methyl carboxylate, i.e., the phenol is methyl 4-hydroxybenzoate. In some embodiments, each of $R_1$, $R_3$, and $R_5$ are hydrogen, one of $R_2$ and $R_4$ is hydrogen, and the other of $R_2$ and $R_4$ is methyl, i.e., the structure is m-cresol. In some embodiments, each of $R_1$, $R_3$, and $R_5$ are hydrogen, one of $R_2$ or $R_4$ is hydrogen, and the other of $R_2$ or $R_4$ is an aromatic heterocycle, such as a pyridine ring, i.e., the structure is 3-(pyridine-2-yl)phenol or 3-(pyridine-3-yl)phenol. In some embodiments, each of $R_1$, $R_4$, and $R_5$ are hydrogen and $R_2$ and $R_3$ form a fused six-membered ring comprising nitrogen, i.e., the phenol is quinolin-6-ol. In some embodiments, $R_1$ is hydrogen, $R_2$ and $R_3$ form a fused six-membered ring, and $R_4$ and $R_5$ form a fused six-membered ring, i.e., the phenol is phenanthren-9-ol.

In the first step for the preparation of the thiocarbonate, specifically, an O,O-diaryl thiocarbonate, the aromatic alcohol is contacted with a thiocarbonyl-containing compound having the following Structure (III):

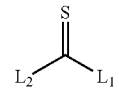

Structure (III)

wherein $L_1$ and $L_2$ are each leaving groups. Preferably, the leaving groups are halides. In a preferred embodiment, each of $L_1$ and $L_2$ are chloride ions such that the thiocarbonyl compound is thiophosgene.

In some embodiments, the aromatic alcohol may be suitably dissolved in aqueous solution, preferably an alkaline aqueous solution, i.e., pH greater than 7. The thiocarbonyl compound is suitably dissolved in an organic solvent. Suitable organic solvents are those that are unreactive to moderately strong nucleophiles and may include dichloromethane (DCM), halogenated solvents, ethers such as diemthyl ether or diethyl ether, tetrahydrofuran, acetonitrile, dimethyl sulfoxide, and dimethylformamide.

The solution comprising the aromatic alcohol having Structure (II) and the solution comprising the thiocarbonyl compound having Structure (III) are mixed under vigorous conditions, e.g., agitation, to allow the respective reactants to contact each other and thereby form an O,O-diaryl thiocarbonate having the following Structure (IV):

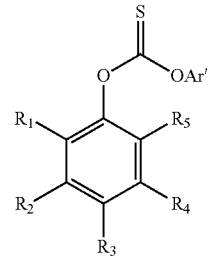

Structure (IV)

wherein $R_1$, $R_2$, $R_3$, $R_4$, and $R_5$ are as defined above in connection with Structure (II). Ar' may be the same or different than the aromatic ring having substituents $R_1$, $R_2$, $R_3$, $R_4$, and $R_5$.

In some embodiments, the thiocarbonate having the above Structure (IV) is a symmetrical thiocarbonate, i.e., both aromatic groups of the aryloxy moieties bonded to the thiocarbonyl (C=S) are identical. In order to prepare symmetrical thiocarbonates, the aromatic alcohol is reacted in substantial molar excess over the thiocarbonyl compound, i.e., in a molar ratio of at least about 1.8:1, preferably at least about 2:1. A symmetrical thiocarbonate may have the following Structure (IVA):

Structure (IVA)

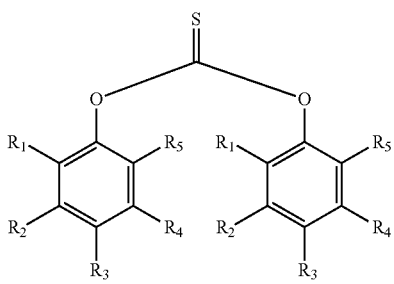

wherein $R_1$, $R_2$, $R_3$, $R_4$, and $R_5$ are as defined above in connection with Structure (II).

In some embodiments, the thiocarbonate having the Structure (IV) is an asymmetrical O,O-diaryl thiocarbonate, i.e., the aromatic groups of the aryloxy moieties bonded to the thiocarbonyl (C=S) are structurally different. In order to prepare an asymmetrical thiocarbonate, two aromatic alcohols are reacted with the thiocarbonyl sequentially. In some embodiments, the reaction sequence to prepare an asymmetrical O,O-diaryl thiocarbonate begins by reacting an aromatic alcohol having Structure (II) with a thiocarbonyl compound having Structure (III) to form an intermediate O-aryl intermediate having the Structure (IVB) below:

Structure (IVB)

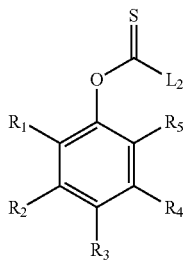

This O-aryl intermediate having Structure (IVB) is then reacted with a second aromatic alcohol to form an asymmetric O,O-diaryl thiocarbonate. For example, the second aromatic alcohol may have Structure (IIA):

Structure (IIA)

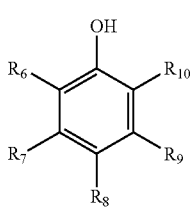

In Structure (IIA), the moieties $R_6$, $R_7$, $R_8$, $R_9$, and $R_{10}$ may be defined in the same manner that the moieties of $R_1$, $R_2$, $R_3$, $R_4$, and $R_5$ are defined in connection with Structure (II) with the proviso that at least one of $R_6$, $R_7$, $R_8$, $R_9$, and $R_{10}$ in the aromatic alcohol having Structure (IIA) is different than at least one of $R_1$, $R_2$, $R_3$, $R_4$, and $R_5$ of the aromatic alcohol having Structure (II). It should be noted that Structure (II) and Structure (IIA) may be equivalent if substituents in the ortho position ($R_1$, $R_5$, $R_6$, and $R_{10}$) or meta position ($R_2$, $R_4$, $R_7$, and $R_9$) are merely reversed. For example, Structures (II) and (IIA) are identical if $R_1$ were hydrogen, $R_5$ were cyano, $R_6$ were cyano, and $R_{10}$ were hydrogen if $R_2$, $R_3$, $R_4$, $R_7$, $R_8$, and $R_9$ were otherwise identical. The structures would differ if, for example, an ortho-cyano group in one structure is not found in either ortho-position on the other structure, all other substituents being equal.

Reaction of the O-aryl intermediate of Structure (IVB) with the aromatic alcohol of Structure (IIA) forms an asymmetrical O,O-diaryl thiocarbonate having Structure (IVC):

Structure (IVC)

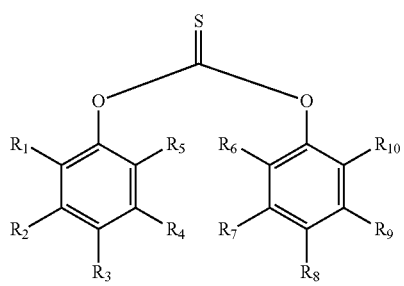

wherein $R_1$, $R_2$, $R_3$, $R_4$, and $R_5$ are as defined above in connection with Structure (II), $R_6$, $R_7$, $R_8$, $R_9$, and $R_{10}$ are as defined above in connection with Structure (IIA), and the structures of the two aryl groups are different.

The general reaction sequence for the preparation of asymmetrical thiocarbonates is depicted below as Scheme (3):

Scheme (3)

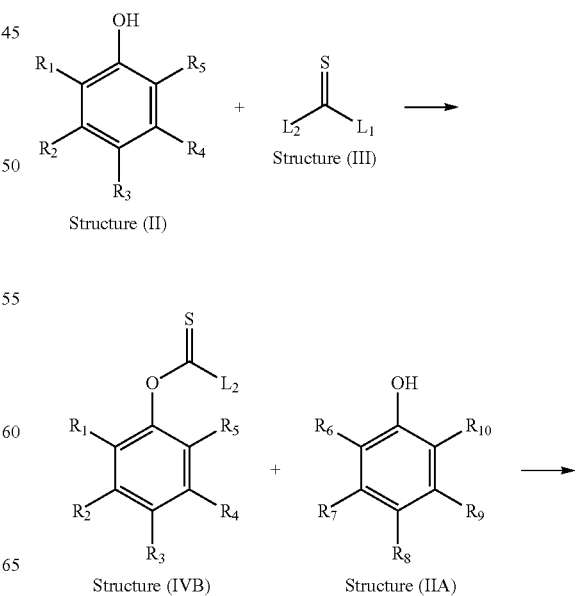

-continued

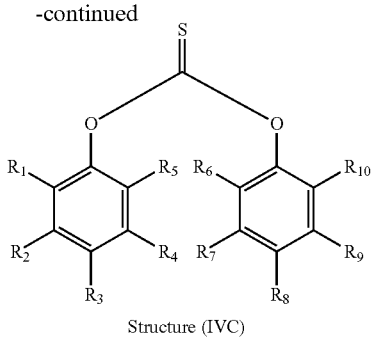

Structure (IVC)

wherein Structure (IIA) depicts a second reacted aromatic alcohol having a different chemical structure than the first reacted aromatic alcohol of Structure (II), such that Structure (IVC) defines an asymmetrical O,O-diaryl thiocarbonate.

In those embodiments wherein an asymmetrical thiocarbonate is formed, the first aromatic alcohol, i.e., of Structure (II), may be reacted in a molar ratio of less than about 0.6:1, preferably about 0.5:1, so that a substantial number of reactive sites remain on the thiocarbonyl compound in the intermediate Structure (IVB). The reaction with the first aromatic alcohol is followed sequentially by reaction with the second aromatic alcohol, i.e., of Structure (IIA).

The thiocarbonate of Structure (IV), whether the symmetrical O,O-diaryl thiocarbonate of Structure (IVA) or the asymmetrical O,O-diaryl thiocarbonate of Structure (IVB), thus formed is subjected to radical catalyzed rearrangement, further explained herein below, to form an aromatic carboxylic acid aryl esters of general Structure (I).

B. Radical Catalyzed Rearrangement of Thiocarbonate to Form Aromatic Carboxylic Acid Aryl Esters In order to effect the rearrangement of an O,O-diaryl thiocarbonate of Structure (IV) into an aromatic carboxylic acid aryl ester (e.g., a benzoic acid aryl ester) of Structure (I), the thiocarbonate of Structure (IV) is contacted with a radical containing reactant that has thiophilicity, i.e., a radical that regioselectively attacks at the sulfur atom of the C=S moiety. Regioselectivity is the preference for one direction of chemical bond making or breaking over other possible directions. In the context of the present invention, a radical is formed that regioselectively attacks at the sulfur atom of the C=S moiety, meaning that the radical forms a bond with the sulfur atom, thereby forming a carbon-centered radical as shown in Scheme (2) above and Scheme (4) below.

Accordingly, in the next step of the method of the present invention, the O,O-diaryl thiocarbonate is thus reacted with a regioselective radical. In some embodiments, the radical that regioselectively reacts with the sulfur atom of the thiocarbonyl moiety comprises an Si- or Sn-centered radical. The Si- or Sn-centered radical results from a reaction between a radical initiator, for example, a peroxide in which the oxygen-oxygen bond is broken yielding two oxygen centered radicals and an Si- or Sn-centered compound that is reactive with the oxygen centered radicals. Si-centered compounds include silanes, preferably a substituted silane substituted with alkyl or aryl moieties. The alkyl moieties are generally short chained having from 1 to 6 carbon atoms, preferably 1 to 4 carbon atoms. The aryl moiety is generally a single ring, e.g., phenyl, or possibly a fused ring, e.g., naphthenyl. The silane generally comprises at least one Si—H group. Useful silanes include, for example, triethyl silane ($Et_3SiH$), tris(trimethylsilyl)silane (TTMSS), diphenyl silane. Sn-centered compounds include stannanes, preferably a substituted stannane substituted with alkyl or aryl moieties. The alkyl moieties are generally short chained having from 1 to 6 carbon atoms, preferably 1 to 4 carbon atoms. The aryl moiety is generally a single ring, e.g., phenyl, or possibly a fused ring, e.g., naphthenyl. The silane generally comprises at least one Sn—H group. Useful stannanes include, for example, tributyl stannane ($Bu_3SnH$).

Useful radical initiators include peroxides and diazenes. Useful peroxides are preferably substituted with alkyl or aryl moieties and may include, for example, benzoyl peroxide, di-tert-butyl peroxide, lauroyl peroxide, 2-butanone peroxide, and di-tert-amyl peroxide. Useful diazenes are preferably substituted with alkyl or aryl moeities and may include, for example, 2,2'-azobis(2-methylpropionitrile), (AIBN) and 1,1'-azobis(cyanocyclohexane) (V-40). In a radical propagation sequence, heating a peroxide initiator breaks the O—O bond in the peroxide thereby yielding two oxygen centered radicals. These radicals abstract a hydrogen atom from either a Si—H or Sn—H bond in the Si- or Sn-centered compounds thus generating a radical which reacts with the thiocarbonate. In some embodiments of the invention, the reaction mixture is heated to a temperature sufficient to break the peroxide or diazene bond. In general, the reaction mixture may be heated to a temperature between about 90° C. and about 150° C. After the initial reaction between the peroxide radical and the Si- or Sn-centered compound to form the radical that regioselectively attacks at the sulfur atom of the C=S moiety, the peroxide does not necessarily participate in further radical formation since the O-neophyl rearrangement involving the C—O transposition sequence is terminated by a fragmentation which generates a new radical capable of reacting with additional silane reagent containing at least one Si—H or additional stannane reagent containing at least one Sn—H, thereby propagating the cycle by converting more molecules of starting material into the product.

The radical initiator (e.g., peroxide or substituted diazene reagent) and the Si- or Sn-centered compound are generally contacted in a molar ratio of peroxide to Si- or Sn-centered compound between about 1:4 and about 2:1, such as between about 1:3 and about 1:1, such as about 1:2.

The Si- or Sn-centered compound and O,O-diaryl thiocarbonate are generally contacted in a molar ratio of Si- or Sn-centered compound to thiocarbonate between about 4:1 and about 1:4, such as between about 3:1 and about 1:1, such as about 3:2.

The reaction may be carried out in a solvent that does not deactivate the intermediate radicals. Exemplary aprotic solvents that may be used include benzene, toluene, trifluoromethyl benzene, chlorobenzene, dimethyl sulfoxide (DMSO), hexamethylphosphoramide (HMPA), tetrahydrofuran (THF), and dimethyl formamide (DMF). Certain protic solvents may be used such as methanol, ethanol, and water. Preferably, protic solvents that may be reactive with the carbon-centered radical (see Scheme (2) above) are avoided.

The proposed mechanism of the transformation of an O,O-diaryl thiocarbonate into an aromatic carboxylic acid aryl ester is depicted in the following Scheme (4):

Scheme (4)

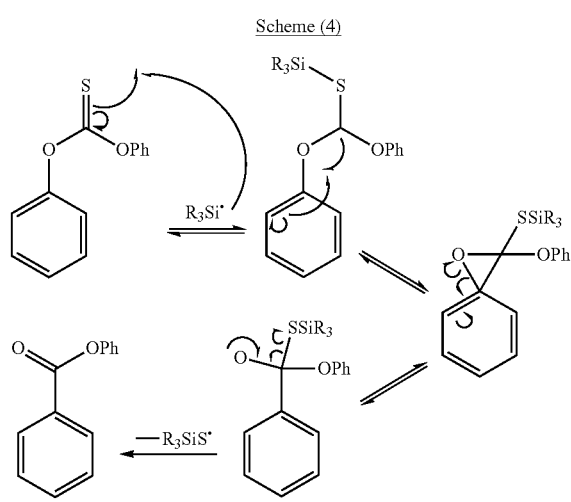

The anomerically stabilized carbon radical center formed by the addition of the silicon radical to the S=C bond follows the same pathway described above in Scheme (1). β-scission that occurs on the S—C results in the formation of the C=O (ester) which is considered as the driving force of this transformation. Substituent effects are consistent with the proposed radical mechanism because both OMe and CN substituents facilitate the rearrangement and show significant selectivity towards substituted aromatic rings (See Table 1). Table 1 summarizes the results from the reaction of different silanes (R₃SiH and TTMSS) with several diaryl thiocarbonates in the presence of di-t-butyl peroxide ("TOOT" in Table 1).

With respect to other aromatics, unlike naphthalene (a polyaromatic group) that shows a fully selective O-neophyl rearrangement, pyridine (a heteroaromatic group) show almost no selectivity compared to phenyl groups. This observation is also consistent with the expectation that the electron poor aromatic ring, pyridine, would not have significant effect on radical pathways as it would have on ionic reactions. Alternatively, the full selectivity observed for the naphthyl group is probably due to the partial loss of aromaticity in the ipso radical attack step compared to the full loss of aromaticity in phenyl groups. It is noteworthy that the choice of substituent Z in Scheme (1) is very important as illustrated by the premature β-scission of the first radical intermediate and subsequent lack of the O-neophyl rearrangement for Z=OMe.

TABLE 1

Results of O-Neophyl Rearrangement/Fragmentation Cascade of Diaryl Thiocarbonates.

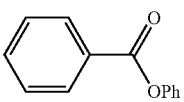

| Ar | R₃SiH | Ar' | Time | A % yield | B % yield |
|---|---|---|---|---|---|
| Ph | TTMSS | Ph | 2 h | 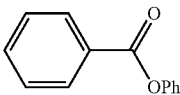 55 | NA |
| Ph | Et₃SiH | Ph | 2 h | 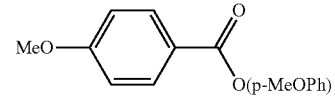 59 | NA |
| p-MeO-Ph | TTMSS | p-MeO-Ph | 2 h | 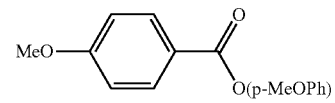 80 | NA |
| p-MeO-Ph | Ph₂SiH₂ | p-MeO-Ph | 2 h | 30 | NA |

TABLE 1-continued

Results of O-Neophyl Rearrangement/Fragmentation Cascade of Diaryl Thiocarbonates.

ArO−C(=S)−OAr' + R$_3$SiH (1.5 eq.), TOOT (0.75 eq.), PhH, (135° C.) → Ar−C(=O)−OAr' (A) + Ar'−C(=O)−OAr (B)

| Ar | R$_3$SiH | Ar' | Time | A % yield | B % yield |
|---|---|---|---|---|---|
| p-MeO-Ph | Et$_3$SiH | p-MeO-Ph | 2 h | MeO-C$_6$H$_4$-C(=O)-O(p-MeOPh); 93 | NA |
| Ph | TTMSS | p-MeO-Ph | 2 h | Ph-C(=O)-O(p-MeOPh); 26 | MeO-C$_6$H$_4$-C(=O)-OPh; 60 |
| Ph | TTMSS | p-MeO-Ph | 50 min | Ph-C(=O)-O(p-MeOPh); 16 | MeO-C$_6$H$_4$-C(=O)-OPh; 63 |
| Ph | Et$_3$SiH | p-MeO-Ph | 2 h | Ph-C(=O)-O(p-MeOPh); 30 | MeO-C$_6$H$_4$-C(=O)-OPh; 61 |
| Ph | Et$_3$SiH | p-MeO-Ph | 1.5 h | Ph-C(=O)-O(p-MeOPh); 16 | MeO-C$_6$H$_4$-C(=O)-OPh; 79 |
| Ph | Et$_3$SiH | p-CNPh | 1.5 h | Ph-C(=O)-O(p-CNPh); 16 | NC-C$_6$H$_4$-C(=O)-OPh; 63 |
| Ph | Et$_3$SiH | p-FPh | 2 h | Ph-C(=O)-O(p-FPh); 31 | F-C$_6$H$_4$-C(=O)-OPh; 31 |
| Ph | Et$_3$SiH | p-BrPh[a,b] | 4 h | Ph-C(=O)-O(p-BrPh); 19 | Br-C$_6$H$_4$-C(=O)-OPh; 27 |
| Ph | Et$_3$SiH | p-NO$_2$Ph | 2-5 h | [c] | — |

TABLE 1-continued

Results of O-Neophyl Rearrangement/Fragmentation
Cascade of Diaryl Thiocarbonates.

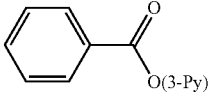

| Ar | R$_3$SiH | Ar' | Time | A % yield | B % yield |
|---|---|---|---|---|---|
| Ph | Et$_3$SiH | 3-Pyridinyl | 4 h | 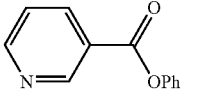 30 | 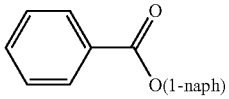 34 |
| Ph | Et$_3$SiH | 1-naphthyl | 2 h | trace | 89 |
| Ph | TTMSS | Me | 2 h | $d$ | NA |
| Ph | Et$_3$SiH | 1-naphthyl | 2 h | 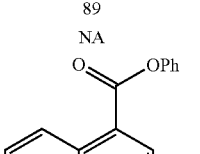 <1 | 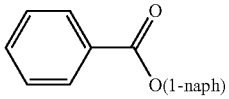 89 |
| Ph | Et$_3$SiH | 2-naphthyl | 5 h | 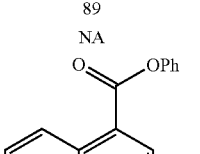 15 | 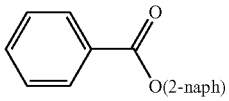 61 |
| Ph | Et$_3$SiH | 6-quinolinyl$^e$ | 12 h | 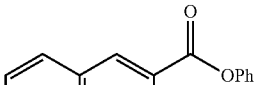 11 | 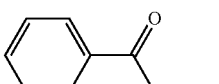 40 |
| Ph | Et$_3$SiH | 9-phenanthryl | 4 h | 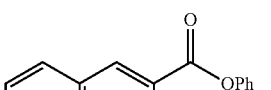 0 | 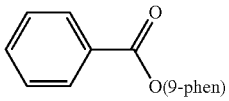 65 |

$^a$3 eq. of Et$_3$SiH and 1.5 eq. of TOOT were used for full conversion of starting material.
$^b$two additional products were formed besides A and B.
$^c$complicated mixture was obtained.
$^d$NMR of reaction mixture showed complete disappearance of methyl signal with no signals of rearrangement product.
$^e$4 eq. of Et$_3$SiH and 2 eq. of TOOT were used for full conversion of starting material.

II. Conversion of Aromatic Alcohol into N-Aryl Aromatic Carboxamide

In some embodiments, the method of the present invention is directed to a method for converting an aromatic alcohol (e.g., a phenol) into an N-aryl aromatic carboxamide (e.g., an N-aryl benzamide) having the following Structure

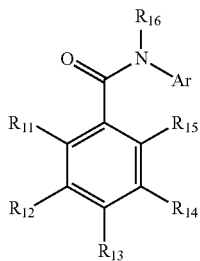

Structure (V)

wherein $R_{11}$, $R_{12}$, $R_{13}$, $R_{14}$, and $R_{15}$ are each independently a hydrogen, an alkyl, an alkenyl, an alkynyl, an alkoxy, a cyano, an aryl, an aromatic heterocycle, an ester, an amino, a hydrazide, an amide, thioether, sulfone, sulfoxide, sulfonic esters, and sulfinic esters, a carboxylate, or a halide. The various moieties that make up $R_1$, $R_2$, $R_3$, $R_4$, and $R_5$ may be substituted or unsubstituted and generally comprise from 0 to about 24 carbon atoms, from one to about 24 carbon atoms, such as from about 1 to about 12 carbon atoms, or from about 1 to about 6 carbon atoms. Exemplary moieties that may contain no carbon include, for example, sulfone, sulfoxide, sulfonic esters, and sulfinic esters, amino, hydrazide, or halides bonded directly to the aromatic ring. Certain of these moieties, e.g., amino, may optionally be substituted with carbon-containing groups, commonly alkyl having from 1 to 12 carbon atoms. The halide may be fluoride, chloride, bromide, or iodide. Exemplary substituents containing one carbon atom include, for example, cyano, methyl, methoxy, and methylamino. Exemplary substituents containing two carbon atoms include, for example, ethyl, ethoxy, ethylamino, dimethylamino, and methylcarboxylate. Exemplary substituents containing three carbon atoms include, for example, n-propyl, isopropyl, n-propoxy, isopropoxy, methylethylamino, and ethylcarboxylate.

Experimental results to date indicate that the O-neophyl reaction is accelerated by substituents which have either a lone pair (e.g., alkoxy (OR) and amino (NRR')) or a π-bond (e.g., cyano (CN)) at the ortho or para position, independent of whether these substituents are donors or acceptors. It has also been observed that substituents at the meta position have very little effect.

In some embodiments, any $R_{11}$, $R_{12}$, $R_{13}$, $R_{14}$, and $R_{15}$ together with an adjacent R group (e.g., $R_{11}$ and $R_{12}$, or $R_{12}$ and $R_{13}$), the atoms to which they are bonded in the aryl group, and additional atoms (not shown) form a cyclic moiety, such as a fused aromatic ring. Exemplary aromatic rings comprising fused ring structures include naphthalene, anthracene, phenanthrene, pyrene, benz(a)anthracene, benzo[c]phenanthrene, tetracene, chrysene, and triphenylene. The additional atoms may comprise nitrogen or oxygen, and the fused ring may be a aromatic heterocyclic ring, such as quinoline, isoquinoline, pyridine, quinoxaline, quinazoline, cinnoline, pyrimidine, acridine, etc.

In some embodiments, any $R_{11}$, $R_{12}$, $R_{13}$, $R_{14}$, and $R_{15}$ may comprise a cyclic structure that is not fused to the ring, for example, a phenyl, a pyridyl, etc.

In the above Structure (V), $R_{16}$ is a hydrogen, a hydrocarbyl, or an aryl. The hydrocarbyl, e.g., alkyl, or aryl generally comprises from one to about 24 carbon atoms, such as from about 1 to about 12 carbon atoms, or from about 1 to about 6 carbon atoms. In some embodiments, the hydrocarbyl is an alkyl such as methyl, ethyl, n-propyl, isopropyl, preferably methyl or ethyl.

In the above Structure (V), Ar denotes an aromatic ring containing moiety, which may be the same or different as the ring depicted in Structure (V) as having substituents $R_{11}$ through $R_{15}$.

A. Preparation of a Thiocarbamate from an Aromatic Alcohol and an Aniline

In the first step of the reaction sequence for the preparation of an N-aryl aromatic carboxamide (e.g., an N-aryl benzamide) having Structure (V), a thiocarbamate is prepared from an aromatic alcohol and an aniline. The aromatic alcohol is reacted with a compound containing thiocarbonyl (C=S) moiety in order to prepare an O-aryl thiocarbonate intermediate. The O-aryl thiocarbonate intermediate is then reacted with an aniline in order to prepare an O-aryl-N-aryl-thiocarbmate containing an aryloxy moiety and an aniline moiety bonded to the thiocarbonyl (C=S) moiety. The sequence may be reversed such that the aniline is reacted with the compound containing thiocarbonyl (C=S) moiety first followed by reaction with the aromatic alcohol. The thiocarbamate thus comprises an O-aryl-N-aryl-thiocarbmate and has a general structure:

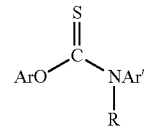

wherein Ar and Ar' are aryl moieties, which aryl moieties may be the same or different, and the additional R substituent bonded to the nitrogen atom may be aryl or alkyl.

The aromatic alcohol may have the following Structure (VI):

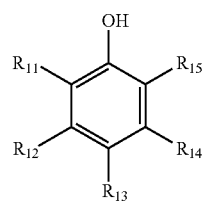

Structure (VI)

wherein $R_{11}$, $R_{12}$, $R_{13}$, $R_{14}$, and $R_{15}$ are each independently a hydrogen, an alkyl, an alkenyl, an alkynyl, an alkoxy, a cyano, an aryl, an aromatic heterocycle, an ester, an amino, a hydrazide, an amide, thioether, sulfone, sulfoxide, sulfonic esters, and sulfinic esters, a carboxylate, or a halide. The various moieties that make up $R_1$, $R_2$, $R_3$, $R_4$, and $R_5$ may be substituted or unsubstituted and generally comprise from 0 to about 24 carbon atoms, from one to about 24 carbon atoms, such as from about 1 to about 12 carbon atoms, or from about 1 to about 6 carbon atoms. Exemplary moieties that may contain no carbon include, for example, sulfone, sulfoxide, sulfonic esters, and sulfinic esters, amino, hydrazide, or halides bonded directly to the aromatic ring. Certain of these moieties, e.g., amino, may optionally be substituted with carbon-containing groups, commonly alkyl having from 1 to 12 carbon atoms. The halide may be fluoride, chloride, bromide, or iodide. Exemplary substituents containing one carbon atom include, for example, cyano, methyl, methoxy, and methylamino. Exemplary substituents containing two carbon atoms include, for example, ethyl, ethoxy, ethylamino, dimethylamino, and methylcarboxylate. Exemplary substituents containing three carbon atoms include, for example, n-propyl, isopropyl, n-propoxy, isopropoxy, methylethylamino, and ethylcarboxylate.

Experimental results to date indicate that the O-neophyl reaction is accelerated by substituents which have either a lone pair (e.g., alkoxy OR, and amino NRR') or a π-bond (e.g., cyano CN) at the ortho or para position, independent of whether these substituents are donors or acceptors. It has also been observed that substituents at the meta position have very little effect.

In some embodiments, any $R_{11}$, $R_{12}$, $R_{13}$, $R_{14}$, and $R_{15}$ together with an adjacent R group (e.g., $R_{11}$ and $R_{12}$, or $R_{12}$ and $R_{13}$), the atoms to which they are bonded in the aryl group, and additional atoms (not shown) form a cyclic moiety, such as a fused aromatic ring. Exemplary aromatic rings comprising fused ring structures include naphthalene, anthracene, phenanthrene, pyrene, benz(a)anthracene, benzo[c]phenanthrene, tetracene, chrysene, and triphenylene. The additional atoms may comprise nitrogen or oxygen, and the fused ring may be a aromatic heterocyclic ring, such as quinoline, isoquinoline, pyridine, quinoxaline, quinazoline, cinnoline, pyrimidine, acridine, etc.

In some embodiments, any $R_{11}$, $R_{12}$, $R_{13}$, $R_{14}$, and $R_{15}$ may comprise a cyclic structure that is not fused to the ring, for example, a phenyl, a pyridyl, etc.

In some embodiments, each of $R_{11}$, $R_{12}$, $R_{13}$, $R_{14}$, and $R_{15}$ is hydrogen, and the aromatic alcohol is phenol. In some embodiments, any $R_{11}$, $R_{12}$, $R_{13}$, $R_{14}$, and $R_{15}$ together with an adjacent R group and the atoms to which they are bonded form a cyclic moiety, such as a 6-membered ring fused to the ring having substituents $R_{11}$, $R_{12}$, $R_{13}$, $R_{14}$, and $R_{15}$, i.e., naphthane-1-ol or naphthane-2-ol. In some embodiments, each of $R_{13}$, $R_{14}$, and $R_{15}$ are hydrogen, and $R_{11}$ and $R_{12}$, together with the carbons to which they are bonded form a 6-membered ring fused to the phenol ring, i.e., naphthane-1-ol. In some embodiments, each of $R_{11}$, $R_{14}$, and $R_{15}$ are hydrogen, and $R_{12}$ and $R_{13}$, together with the carbons to which they are bonded form a 6-membered ring fused to the phenol ring, i.e., naphthane-2-ol. In some embodiments, each of $R_{11}$, $R_{12}$, $R_{14}$, and $R_{15}$ are hydrogen, and $R_{13}$ is an alkoxy moiety, preferably a methoxy, ethoxy, n-propoxy, or isopropoxy. In some preferred embodiments, the alkoxy is a methoxy, i.e., the structure is 4-methoxyphenol. In some embodiments, each of $R_{11}$, $R_{12}$, $R_{14}$, and $R_{15}$ are hydrogen, and $R_3$ is a cyano, i.e., the structure is 4-hydroxybenzonitrile. In some embodiments, each of $R_{11}$, $R_{12}$, $R_{14}$, and $R_{15}$ are hydrogen, and $R_{13}$ is a chloride, i.e., the structure is 4-chlorophenol. In some embodiments, each of $R_{11}$, $R_{12}$, $R_{14}$, and $R_{15}$ are hydrogen, and $R_{13}$ is a bromide, i.e., the structure is 4-bromophenol. In some embodiments, each of $R_{11}$, $R_{12}$, $R_{14}$, and $R_{15}$ are hydrogen, and $R_{13}$ is a fluoride, i.e., the structure is 4-fluorophenol. In some embodiments, each of $R_1$, $R_2$, $R_4$, and $R_5$ are hydrogen, and $R_{13}$ is methyl, i.e., the structure is p-cresol. In some embodiments, each of $R_{11}$, $R_{12}$, $R_{14}$, and $R_{15}$ are hydrogen, and $R_{13}$ is phenyl, i.e., the structure is [1,1'-biphenyl]-4-ol. In some embodiments, each of $R_{11}$, $R_{12}$, $R_{14}$, and $R_{15}$ are hydrogen, and $R_{13}$ is methyl carboxylate, i.e., the phenol is methyl 4-hydroxybenzoate. In some embodiments, each of $R_{11}$, $R_{13}$, and $R_{15}$ are hydrogen, one of $R_{12}$ or $R_{14}$ is hydrogen, and the other of $R_{12}$ or $R_{14}$ is methyl, i.e., the structure is m-cresol. In some embodiments, each of $R_{11}$, $R_{13}$, and $R_{15}$ are hydrogen, one of $R_{12}$ or $R_{14}$ is hydrogen, and the other of $R_{12}$ or $R_{14}$ is an aromatic heterocycle, such as a pyridine ring, i.e., the structure is 3-(pyridine-2-yl)phenol or 3-(pyridine-3-yl)phenol. In some embodiments, each of $R_{11}$, $R_{14}$, and $R_{15}$ are hydrogen and $R_{12}$ and $R_{13}$ form a fused six-membered ring comprising nitrogen, i.e., the phenol is quinolin-6-ol. In some embodiments, $R_{11}$ is hydrogen, $R_{12}$ and $R_{13}$ form a fused six-membered ring, and $R_{14}$ and $R_{15}$ form a fused six-membered ring, i.e., the phenol is phenanthren-9-ol.

In some embodiments, the preparation of the O-aryl-N-aryl thiocarbamate occurs by first contacting an aromatic alcohol with a thiocarbonyl compound having the following Structure (VII):

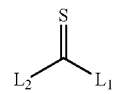

Structure (VII)

wherein $L_1$ and $L_2$ are each leaving groups. In some embodiments, the leaving groups are halides. In a preferred embodiment, each of $L_1$ and $L_2$ are chloride ions such that the thiocarbonyl compound is thiophosgene.

In some embodiments, the aromatic alcohol may be suitably dissolved in aqueous solution, preferably an alkaline aqueous solution, i.e., pH greater than 7. The thiocarbonyl compound is suitably dissolved in an organic solvent. Suitable organic solvents are those that are unreactive to moderately strong nucleophiles and may include dichloromethane (DCM), halogenated solvents, ethers, tetrahydrofuran, acetonitrile, dimethyl sulfoxide, and dimethylformamide.

The aromatic alcohol and thiocarbonyl compound, respectively, are present in the reaction mixture in a molar ratio of less than 0.6:1, preferably about 0.5:1, thereby leaving a substantial number of reactive sites on the thiocarbonyl structure.

The aqueous solution comprising the aromatic alcohol of Structure (VI) and the organic solution comprising the thiocarbonyl compound of Structure (VII) are mixed under vigorous conditions, e.g., agitation, to allow the respective reactants to contact each other and thereby form an O-aryl intermediate product having the following Structure (VIII):

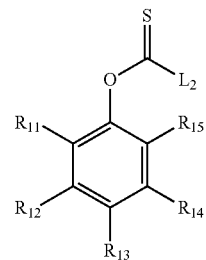

Structure (VIII)

The O-aryl intermediate product having the Structure (VIII) is thereafter contacted with an aniline having the Structure (IX):

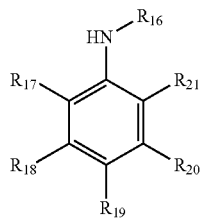

Structure (IX)

wherein $R_{17}$, $R_{18}$, $R_{19}$, $R_{20}$, and $R_{21}$ are each independently a hydrogen, an alkyl, an alkenyl, an alkynyl, an alkoxy, a cyano, an aryl, an aromatic heterocycle, an ester, an amino, a hydrazide, an amide, thioether, sulfone, sulfoxide, sulfonic esters, and sulfinic esters, a carboxylate, or a halide. The various moieties that make up $R_1$, $R_2$, $R_3$, $R_4$, and $R_5$ may be substituted or unsubstituted and generally comprise from 0 to about 24 carbon atoms, from one to about 24 carbon atoms, such as from about 1 to about 12 carbon atoms, or from about 1 to about 6 carbon atoms. Exemplary moieties that may contain no carbon include, for example, sulfone, sulfoxide, sulfonic esters, and sulfinic esters, amino, hydrazide, or halides bonded directly to the aromatic ring. Certain of these moieties, e.g., amino, may optionally be substituted with carbon-containing groups, commonly alkyl having from 1 to 12 carbon atoms. The halide may be fluoride, chloride, bromide, or iodide. Exemplary substituents containing one carbon atom include, for example, cyano, methyl, methoxy, and methylamino. Exemplary substituents containing two carbon atoms include, for example, ethyl, ethoxy, ethylamino, dimethylamino, and methylcarboxylate. Exemplary substituents containing three carbon atoms include, for example, n-propyl, isopropyl, n-propoxy, isopropoxy, methylethylamino, and ethylcarboxylate.

Experimental results to date indicate that the O-neophyl reaction is accelerated by substituents which have either a lone pair (e.g., alkoxy OR, and amino NRR') or a π-bond (e.g., cyano CN) at the ortho or para position, independent of whether these substituents are donors or acceptors. It has also been observed that substituents at the meta position have very little effect.

In some embodiments, any $R_{17}$, $R_{18}$, $R_{19}$, $R_{20}$, and $R_{21}$ together with an adjacent R group (e.g., $R_{17}$ and $R_{18}$, or $R_{18}$ and $R_{19}$), the atoms to which they are bonded in the aryl group, and additional atoms (not shown) form a cyclic moiety, such as a fused aromatic ring. Exemplary aromatic rings comprising fused ring structures include naphthalene, anthracene, phenanthrene, pyrene, benz(a)anthracene, benzo[c]phenanthrene, tetracene, chrysene, and triphenylene. The additional atoms may comprise nitrogen or oxygen, and the fused ring may be a aromatic heterocyclic ring, such as quinoline, isoquinoline, pyridine, quinoxaline, quinazoline, cinnoline, pyrimidine, acridine, etc.

In some embodiments, any $R_{17}$, $R_{18}$, $R_{19}$, $R_{20}$, and $R_{21}$ may comprise a cyclic structure that is not fused to the ring, for example, a phenyl, a pyridyl, etc.

In the above Structure (IX), $R_{16}$ is a hydrogen, a hydrocarbyl, or an aryl. The hydrocarbyl, e.g., alkyl, or aryl generally comprises from one to about 24 carbon atoms, such as from about 1 to about 12 carbon atoms, or from about 1 to about 6 carbon atoms. In some embodiments, the hydrocarbyl is an alkyl such as methyl, ethyl, n-propyl, isopropyl, preferably methyl or ethyl.

In some embodiments, the order of reaction may be reversed such that the thiocarbonyl compound is first reacted with the aniline, followed by addition of the aromatic alcohol. In either event, a thiocarbamate is formed comprising two aryl groups, an aryloxy moiety and an aniline moiety. The thiocarbamate is thus an O-aryl-N-aryl thiocarbamate having the Structure (X):

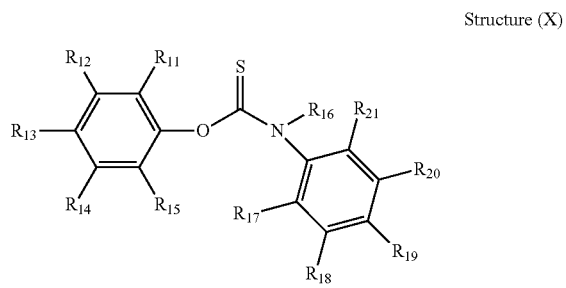

Structure (X)

wherein $R_{11}$, $R_{12}$, $R_{13}$, $R_{14}$, and $R_{15}$ are as defined above in connection with Structure (VI) and $R_{16}$, $R_{17}$, $R_{18}$, $R_{19}$, $R_{20}$, and $R_{21}$ are as defined above in connection with Structure (IX).

To form the N-aryl aromatic carboxamide (e.g., an N-aryl benzamide) having the Structure (V), the O-aryl-N-aryl thiocarbamate of Structure (X) thus formed is subjected to radical catalyzed rearrangement, further explained herein below.

B. Radical Catalyzed Rearrangement of Thiocarbamate to form Aryl Carboxamide

Since unsymmetrical diaryl thiocarbonates show some selectivity during rearrangement into aromatic carboxylic acid aryl esters, the O-neophyl rearrangement reaction was also tested on O-aryl-N-aryl thiocarbamates. In order to effect the rearrangement of a thiocarbamate of Structure (X) into an N-aryl aromatic carboxamide (e.g., an N-aryl benzamide) of Structure (V), the O-aryl-N-aryl thiocarbamate of Structure (X) is contacted with a radical containing reactant that has thiophilicity, i.e., a radical that regioselectively attacks at the sulfur atom of the C=S moiety. In the next step of the method of the present invention, the O-aryl-N-aryl thiocarbamate is thus reacted with a Si- or Sn-centered radical. The Si- or Sn-centered radical results from a reaction between a radical initiator, for example, a peroxide in which the oxygen-oxygen bond is broken yielding two oxygen centered radicals, and an Si- or Sn-centered compound that is reactive with the oxygen centered radicals. Si-centered compounds include silanes, preferably a substituted silane substituted with alkyl or aryl moieties. The alkyl moieties are generally short chained having from 1 to 6 carbon atoms, preferably 1 to 4 carbon atoms. The aryl moiety is generally a single ring, e.g., phenyl, or possibly a fused ring, e.g., naphthenyl. The silane generally comprises at least one Si—H group. Useful silanes include, for example, triethyl silane ($Et_3SiH$), tris(trimethylsilyl)silane (TTMSS), diphenyl silane. Sn-centered compounds include stannanes, preferably a substituted stannane substituted with alkyl or aryl moieties. The alkyl moieties are generally short chained having from 1 to 6 carbon atoms, preferably 1 to 4 carbon atoms. The aryl moiety is generally a single ring, e.g., phenyl, or possibly a fused ring, e.g., naphthenyl. The silane generally comprises at least one Sn—H group. Useful stannanes include, for example, tributyl stannane (Bu₃SnH).

Useful radical initiators include peroxides and diazenes. Useful peroxides are preferably substituted with alkyl or aryl moieties and may include, for example, benzoyl peroxide, di-tert-butyl peroxide, lauroyl peroxide, 2-butanone peroxide, and di-tert-amyl peroxide. Useful diazenes are preferably substituted with alkyl or aryl moeities and may include, for example, 2,2'-azobis(2-methylpropionitrile), (AIBN) and 1,1'-azobis(cyanocyclohexane) (V-40). In a radical propagation sequence, heating a peroxide initiator breaks the O—O bond in the peroxide thereby yielding two oxygen centered radicals. These radicals abstract a hydrogen atom from either a Si—H or Sn—H bond in the Si- or Sn-centered compounds thus generating a radical which reacts with the thiocarbamate. In some embodiments of the invention, the reaction mixture is heated to a temperature sufficient to break the peroxide or diazene bond. In general, the reaction mixture may be heated to a temperature between about 90° C. and about 150° C. After the initial reaction between the peroxide radical and the Si- or Sn-centered compound to form the radical that regioselectively attacks at the sulfur atom of the C=S moiety, the peroxide does not necessarily participate in further radical formation since the O-neophyl rearrangement involving the C—O transposition sequence is terminated by a fragmentation which generates a new radical capable of reacting with additional silane reagent containing at least one Si—H or additional stannane reagent containing at least one Sn—H, thereby propagating the cycle by converting more molecules of starting material in the product.

The radical initiator (e.g., peroxide or substituted diazene reagent) and the Si- or Sn-centered compound are generally contacted in a molar ratio of peroxide to Si- or Sn-centered compound between about 1:4 and about 2:1, such as between about 1:3 and about 1:1, such as about 1:2.

The Si- or Sn-centered compound and O-aryl-N-aryl-thiocarbamate are generally contacted in a molar ratio of Si- or Sn-centered compound to thiocarbonate between about 4:1 and about 1:4, such as between about 3:1 and about 1:1, such as about 3:2.

The reaction may be carried out in a solvent that does not deactivate the intermediate radicals. Exemplary aprotic solvents that may be used include benzene, toluene, trifluoromethyl benzene, chlorobenzene, dimethyl sulfoxide (DMSO), hexamethylphosphoramide (HMPA), tetrahydrofuran (THF), and dimethyl formamide (DMF). Certain protic solvents may be used such as methanol, ethanol, and water. Preferably, protic solvents that may be reactive with the carbon-centered radical (see Scheme (2) above) are avoided.

In the preparation of aromatic carboxylic acid aryl esters, Et₃SiH is a preferred Si-centered radical since it showed reactions with higher yields with thiocarbonates. N,N-diethylphenyl thiocarbamate was treated under the same conditions as the thiocarbonates with 0% conversion of starting material even after heating for 4 hours at 135° C. Without being bound by a particular theory, the lack of reactivity may be due to excessive stabilization of the anomeric radical by the hyperconjugative interaction with the adjacent nitrogen lone pair and that donor ability of the nitrogen atom can be moderated by the presence of an aromatic substituent. Indeed, the reaction of diaryl thiocarbamates did not only result in good yields of the neophyl rearrangement product, but also complete selectivity towards the formation of the corresponding amides. As it is shown in Table 2, double the time and the amounts of reagents were needed for a complete thiocarbamate conversion into the amide product with excellent to good yields. In this case, 2,2'-ditertbutylperoxy butane (DTBPB) was used instead of TOOT in order to obtain higher yields of rearranged products according to our optimized conditions. Table 2 summarizes the results from the reaction of triethyl silane (Et₃SiH) with several thiocarbamates in the presence of 2,2'-ditertbutylperoxy butane (DTBPB).

TABLE 2

Results of O-Neophyl Rearrangement/Fragmentation Cascade of Thiocarbamates

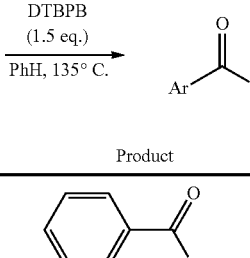

| Entry | Ar | Time (h) | Product | Yield [%] |
|---|---|---|---|---|
| 1 | Ph | 4 | 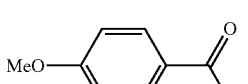 | 88 |
| 2 | p-MeOPh | 4 | 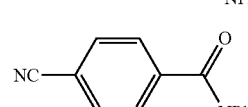 | 80 |
| 3 | p-CNPh | 4 | 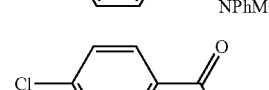 | 75 |
| 4 | p-ClPh | 4 | 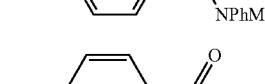 | 63 |
| 5 | p-MePh | 4 | 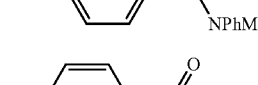 | 72 |
| 6 | m-MePh | 4 | 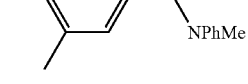 | 76 |
| 7 | p-PhPh | 4 | 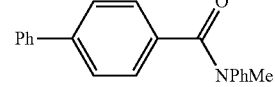 | >99 |
| 8 | p-(MeO₂C)Ph | 4 |  | 97 |

TABLE 2-continued

Results of O-Neophyl Rearrangement/Fragmentation Cascade of Thiocarbamates

| Entry | Ar | Time (h) | Product | Yield [%] |
|---|---|---|---|---|
| 9 | 1-naphthyl | 4 | 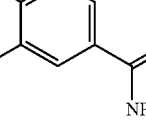 | 98 |
| 10 | 2-naphthyl | 3.5 | 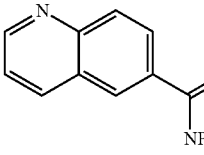 | 77 |
| 11 | 6-quinolinyl | 9 | 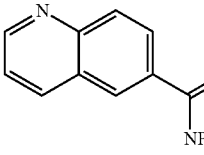 | 57 |

In summary, the present invention is directed to a new, efficient and convenient procedure for the transformations of aromatic alcohols, e.g., phenols, into esters and amides of respective aromatic carboxylic acids.

Having described the invention in detail, it will be apparent that modifications and variations are possible without departing from the scope of the invention defined in the appended claims.

EXAMPLES

The following non-limiting examples are provided to further illustrate the present invention.

General Information Regarding the Synthesis of Thiocarbonates

All starting materials were purchased from Sigma Aldrich and used without further purification. All NMR spectra were collected on a Bruker NMR spectrometer operated at 400 MHz for $^1$H NMR and 100 MHz for $^{13}$C NMR using CDCl$_3$ as solvent. Infrared (IR) spectroscopy was performed using a nitrogen purged FTIR (Nicolet Nexus 470 with a DIGS detector) spectrometer. High resolution mass spectrometry data were collected on a Jeol JMS-600H.

The following depicts the general reaction sequence for the synthesis of thiocarbonates:

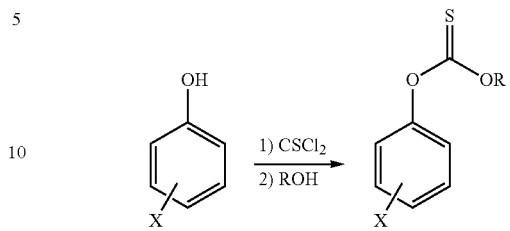

1) X = H, R = Phenyl
2) X = p-methoxy, R = p-methoxyphenyl
3) X = H, R = p-methoxyphenyl
4) X = H, R = p-cyanophenyl
5) X = H, R = p-fluorophenyl
6) X = H, R = p-bromophenyl
7) X = H, R = p-nitrophenyl
8) X = H, R = 3-Pyridinyl
9) X = H, R = Ethyl
10) X = H, R = 3-(4-methoxyphenyl)propyl
11) X = H, R = 1-naphthyl
12) X = H, R = 2-naphthyl
13) X = H, R = 6-quinolinyl
14) X = H, R = 9-phenanthryl General Procedure for the Synthesis of Symmetrical O,O-Diaryl Thiocarbonates.

Phenol (2.4 mmol) was dissolved in 8 mL of aqueous NaOH (0.3 M) and added to a solution of thiophosgene, CSCl$_2$ (1.2 mmol) in 10 mL of dichloromethane (CH$_2$Cl$_2$, 0.5 eq.). The reaction solution (two layers) was stirred vigorously for two hours and then diluted with CH$_2$Cl$_2$, washed with brine, dried with sodium sulfate, Na$_2$SO$_4$. Solvent was removed under reduced pressure and crude mixture was purified by column chromatography to afford the corresponding thiocarbonate.

The above procedure was used to prepare O,O-bisphenyl thiocarbonate (1) as shown below:

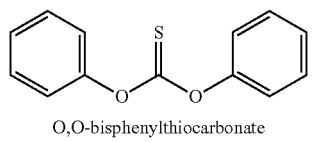 [SMILES: S=C(Oc1ccccc1)Oc1ccccc1]

O,O-bisphenylthiocarbonate

Additional symmetric O,O-diaryl thiocarbonates were prepared according to the above procedure as shown in certain Examples below.

General Procedures for the Synthesis of Nonsymmetrical O,O-Diaryl Thiocarbonates.

Procedure A. The first phenol (1.2 mmol) was dissolved in 4 mL of aqueous 0.3 M NaOH and added to a 10 mL dichloromethane, CH$_2$Cl$_2$ solution of thiophosgene, CSCl$_2$ (1.8 mmol). The two layers were stirred vigorously for one hour. Reaction mixture was diluted with CH$_2$Cl$_2$ and washed with brine. Organic layers were combined and dried with sodium sulfate, Na$_2$SO$_4$ and solvent and excess of CSCl$_2$ were removed under reduced pressure. Reaction mixture was then redissolved in 10 mL of CH$_2$Cl$_2$. The second phenol (1.2 mmol) was then dissolved in 4 mL of 0.3 M NaOH$_{(aq)}$ and added to the above CH$_2$Cl$_2$ solution of the reaction mixture and stirred for two hours. The reaction was then worked up in the same way as before and purified by column chromatography to afford the corresponding thiocarbonate.

Procedure B. The first phenol (1.2 mmol) and thiophosgene, CSCl$_2$ (1.8 mmol) were dissolved in 10 mL of dichloromethane, CH$_2$Cl$_2$ and stirred at 0° C. Neat pyridine (1.5 mmol) was then added dropwise at 0° C. The reaction mixture was left to warm up to room temperature for 15 minutes upon stirring, diluted with CH$_2$Cl$_2$ and washed with brine. Organic layers were combined and dried with Na$_2$SO$_4$. Solvent and excess of CSCl$_2$ were removed under reduced pressure. Reaction mixture and the second phenol (1.2 mmol) were dissolved in 10 mL of CH$_2$Cl$_2$ and stirred at the room temperature. Neat pyridine (1.5 mmol) was added dropwise to the reaction mixture at room temperature. The reaction mixture was stirred for 30 minutes, worked up in the same way as above and purified by column chromatography to afford the corresponding thiocarbonate.

Procedure C. The aromatic alcohol (1.2 mmol) and PhOCSCl (1.8 mmol) were dissolved in 10 mL of CH$_2$Cl$_2$ or MeCN. CsF-Celite (2.4 mmol) was then added to form a heterogeneous mixture. The reaction mixture was stirred at room temperature for 2-6 hours and monitored by TLC. Then reaction mixture was diluted with CH$_2$Cl$_2$ and washed with brine. Organic layers were combined and dried with Na$_2$SO$_4$ and solvent was removed under reduced pressure. The crude mixture was purified by column chromatography to afford the corresponding thiocarbonate.

General Procedures for the Synthesis of O-Aryl-N-Aryl Thiocarbamates.

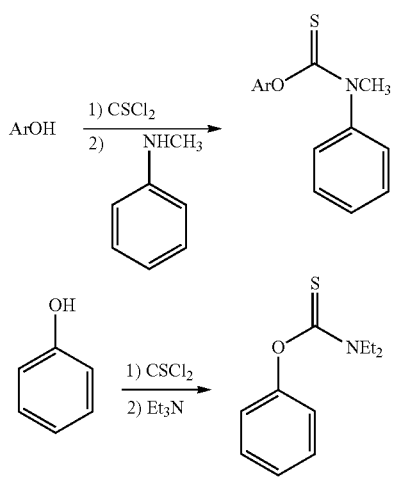

19) Ar = phenyl
20) Ar = p-methoxyphenyl
21) Ar = p-cyanophenyl
22) Ar = p-methylphenyl
23) Ar = m-methylphenyl
24) Ar = p-chlorophenyl
25) Ar = p- (methoxycarbonyl) Ph
26) Ar = p-phenyl-phenyl
27) Ar = 1-naphthyl
28) Ar = 2-naphthyl
29) Ar = 6-quinolinyl Procedure D. The phenol (1.2 mmol) was dissolved in 4 mL of aqueous 0.3 M NaOH and added to a 10 mL dichloromethane, CH$_2$Cl$_2$ solution of thiophosgene, CSCl$_2$ (1.8 mmol). The two layers were stirred vigorously for one hour. Reaction mixture was diluted with CH$_2$Cl$_2$ and washed with brine. Organic layer was dried with Na$_2$SO$_4$ and solvent and excess of CSCl$_2$ were removed under reduced pressure. Reaction mixture was then redissolved in 10 mL of CH$_2$Cl$_2$. Neat N-methyl aniline (2.4 mmol) was then added to the above CH$_2$Cl$_2$ solution of the reaction mixture and stirred for 10 minutes. The reaction was then diluted with CH$_2$Cl$_2$, washed with brine followed by 10 mL of 0.1N HCl$_{aq}$. The organic layer was dried with Na$_2$SO$_4$. Solvent was removed under reduced pressure and the crude mixture was purified by column chromatography to afford the corresponding thiocarbamate.

Procedure E. The phenol (1.2 mmol) and thiophosgene, CSCl$_2$ (1.8 mmol) were dissolved in 10 mL of dichloromethane, CH$_2$Cl$_2$ and stirred at 0° C. Neat pyridine (1.5 mmol) was then added dropwise at 0° C. The reaction mixture was left to warm up to room temperature for 15 minutes upon stirring, diluted with CH$_2$Cl$_2$ and washed with brine. Organic layer was dried with Na$_2$SO$_4$. Solvent and excess of CSCl$_2$ were removed under reduced pressure. Reaction mixture was dissolved in 10 mL of CH$_2$Cl$_2$ and stirred at the room temperature. Neat N-methyl aniline (2.4 mmol) was then added to the above CH$_2$Cl$_2$ solution of the reaction mixture and stirred for 10 minutes. The reaction was then diluted with CH$_2$Cl$_2$, washed with brine followed by 20 mL of 0.1N HCl$_{aq}$ and dried with Na$_2$SO$_4$. Solvent was removed under reduced pressure and the obtained crude mixture was purified by column chromatography to afford the corresponding thiocarbamate.

Procedure F. The aromatic alcohol (1.2 mmol) and Ph(Me)NCSCl (1.8 mmol) were dissolved in 10 mL of CH$_2$Cl$_2$ or ethyl acetate (EtOAC). Triethylamine (Et$_3$N, 2.4 mmol) was then added and reaction mixture was stirred at room temperature (or at reflux) for 12 hours and monitored by TLC. Then reaction mixture was diluted with CH$_2$Cl$_2$ or EtOAC and washed with brine. Organic layers were combined and dried with Na$_2$SO$_4$ and solvent was removed under reduced pressure. The crude mixture was purified by column chromatography to afford the corresponding thiocarbonate.

Ph(Me)NCSCl. N-methyl aniline (3 mmol) was dissolved in 10 mL of CH$_2$Cl$_2$ and added dropwise to a 5 mL CH$_2$Cl$_2$ solution of CSCl$_2$ (1.5 mmol) at 0° C. Then reaction mixture was diluted with CH$_2$Cl$_2$ and washed with brine. Organic layers were combined and dried with Na$_2$SO$_4$ and solvent was removed under reduced pressure. The crude mixture was directly used in the preceding synthesis step.

General Procedure for the O-Neophyl Rearrangement/Fragmentation Reaction.

The thiocarbonates and thiocarbamates prepared according to the above-described above were subjected to the O-neophyl rearrangement according to the following protocol. R$_3$SiH (Triethylsilane, Et$_3$SiH) and peroxide (di-t-butyl peroxide, TOOT) were added to a 15 µM benzene solution of the starting material (thiocarbonate or thiocarbamate). The solution was then bubbled with N$_2$ for 15 minutes, sealed in an Ace Glass pressure tube or thick-walled Pyrex tube, and then heated at 135° C. in an oil bath. Solvent was evaporated and product was purified by chromatography.

General Procedure for the Synthesis of Aryl Benzoates.

Phenol (0.214 mmol) and benzoyl chloride (0.221 mmol) were dissolved in 6 mL of dichloromethane/triethylamine (DCM/Et$_3$N, 5:1) mixture and stirred for one hour. Then reaction solution was diluted with DCM, washed with brine, dried with Na$_2$SO4 and dried under reduced pressure. The crude reaction mixture was purified by column chromatography.

Example 1

O,O-Bis(4-methoxyphenyl)thiocarbonate (2)

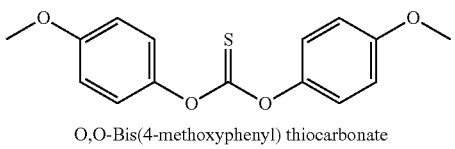

O,O-Bis(4-methoxyphenyl) thiocarbonate

Symmetrical O,O-diaryl thiocarbonate; White solid, mp 161-163° C.; 76%. $^1$H-NMR (400 MHz, CDCl$_3$) δ 7.07 (4H, d, J=9.1 Hz), 6.89 (4H, d, J=9.1 Hz), 3.77 (6H, s); $^{13}$C-NMR (100 MHz, CDCl$_3$) δ 196.1, 158.0, 147.4, 122.7, 114.7, 55.7; IR (KBr) 3051, 2960, 2837, 1883, 1780, 1646, 1601, 1512, 1501, 1456, 1301, 1270, 1244, 1184, 1100, 1035 cm$^{-1}$; HRMS (EI+) calcd for C$_{15}$H$_{14}$O$_4$S 290.06128, found 290.06040.

Example 2

O-(4-Methoxyphenyl)-O-phenyl thiocarbonate (3)

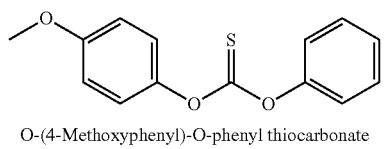 [SMILES: COc1ccc(OC(=S)Oc2ccccc2)cc1]

O-(4-Methoxyphenyl)-O-phenyl thiocarbonate

Procedure A; white solid, mp 109-111° C.; 81%. $^1$H-NMR (400 MHz, CDCl$_3$) δ 7.47 (2H, t, J=7.5 Hz), 7.33 (1H, m), 7.23 (2H, m), 7.15 (2H, d, J=9.1 Hz), 6.96 (2H, d, J=9.1 Hz), 3.83 (3H, s); $^{13}$C-NMR (100 MHz, CDCl$_3$) δ 195.6, 158.1, 153.8, 147.4, 129.8, 127.0, 122.7, 122.0, 114.7, 55.7; IR (KBr) 3051, 2958, 2837, 1882, 1591, 1507, 1489, 1455, 1300, 1282, 1259, 1241, 1181, 1099, 1068, 1035, 1001 cm$^{-1}$; HRMS (EI+) calcd for C$_{14}$H$_{12}$O$_3$S 260.05072, found 260.05061.

Example 3

O-(4-Cyanophenyl)-O-phenyl thiocarbonate (4)

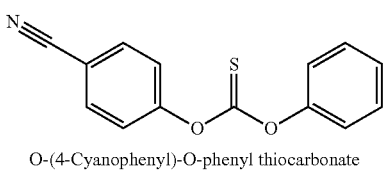 [SMILES: N#Cc1ccc(OC(=S)Oc2ccccc2)cc1]

O-(4-Cyanophenyl)-O-phenyl thiocarbonate

Procedure A; white solid; mp 157-159° C.; 75%. $^1$H-NMR (400 MHz, CDCl$_3$) δ 7.77 (2H, d, J=8.8 Hz), 7.48 (2H, t, J=7.6 Hz), 7.35 (3H, m), 7.22 (2H, m); $^{13}$C-NMR (100 MHz, CDCl$_3$) δ 193.7, 156.3, 153.5, 134.1, 130.0, 127.3, 123.6, 121.8, 118.1, 111.2; IR (KBr) 3096, 3056, 2923, 2234, 1598, 1504, 1491, 1455, 1409, 1284, 1264, 1234, 1209, 1196, 1156, 1103, 1067 cm$^{-1}$; HRMS (EI+) calcd for C$_{14}$H$_9$O$_2$NS 255.03540, found 255.03449.

Example 4

O-(4-Fluorophenyl)-O-phenyl thiocarbonate (5)

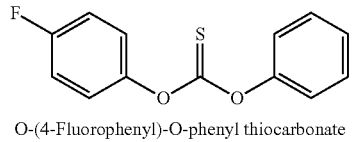 [SMILES: Fc1ccc(OC(=S)Oc2ccccc2)cc1]

O-(4-Fluorophenyl)-O-phenyl thiocarbonate

Procedure A; white solid, mp 108-112° C.; 78%. $^1$H-NMR (400 MHz, CDCl$_3$) δ 7.48 (2H, t, J=7.5 Hz), 7.34 (1H, m), 7.3-7.1 (6H, m); $^{13}$C-NMR (100 MHz, CDCl$_3$) δ 194.8, 160.8 (d, J=244.6 Hz), 153.5, 149.3, 129.7, 126.9, 123.3 (d, J=8.6 Hz), 121.7, 116.3 (d, J=23.7 Hz); IR (KBr) 3072, 3050, 1888, 1653, 1614, 1598, 1506, 1491, 156, 1415, 1290, 1278, 1243, 1176, 1147, 1088, 1068, 1002, 931, 911, 845, 827, 810, 776, 757, 738, 709, 695, 626, 603, 506, 492 cm$^{-1}$; HRMS (EI+) calcd for C$_{13}$H$_9$O$_2$SF 248.03073, found 248.03009.

Example 5

O-(4-Bromophenyl)-O-phenyl thiocarbonate (6)

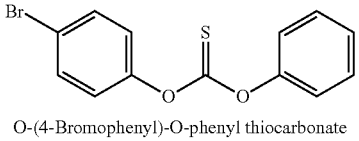 [SMILES: S=C(Oc1ccccc1)Oc1ccc(Br)cc1]

O-(4-Bromophenyl)-O-phenyl thiocarbonate

Procedure A; white solid, mp 134-136° C.; 81%. $^1$H-NMR (400 MHz, CDCl$_3$) δ 7.58 (2H, d, J=8.9 Hz), 7.47 (2H, t, J=7.4 Hz), 7.34 (1H, m), 7.22 (2H, m), 7.12 (2H, d, J=8.9 Hz); $^{13}$C-NMR (100 MHz, CDCl$_3$) δ 194.5, 153.7, 152.6, 132.9, 129.9, 127.1, 123.9, 121.9, 120.3; IR (KBr) 3071, 3050, 2919, 2850, 1948, 1899, 1878, 1746, 1661, 1598, 1485, 1456, 1397, 1376, 1309, 1283, 1244, 1231, 1209, 1191, 1164, 1093, 1067, 1014, 1002, 931, 913, 938, 795, 775, 722, 704, 691, 633, 611, 540, 494, 411, 403 cm$^{-1}$; HRMS (EI+) calcd for C$_{13}$H$_9$O$_2$SBr 307.95066, found 307.95011.

Example 6

O-(4-Nitrophenyl)-O-phenyl thiocarbonate (7)

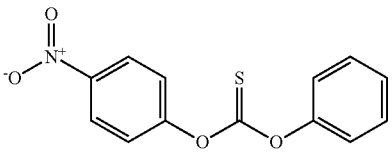

O-(4-Nitrophenyl)-O-phenyl thiocarbonate

Procedure A; white solid, mp 158-162° C.; 74%. $^1$H-NMR (400 MHz, CDCl$_3$) δ 8.35 (2H, d, J=9.1 Hz), 7.48 (2H, m), 7.41 (2H, d, J=9.1 Hz), 7.36 (1H, m), 7.23 (2H, m); $^{13}$C-NMR (100 MHz, CDCl$_3$) δ 193.6, 157.7, 153.5, 146.3, 130.0, 127.3, 125.6, 123.4, 121.8; IR (KBr) 3076, 1614, 1592, 1529, 1487, 1456, 1353, 1288, 1269, 1245, 1155, 1098, 1066, 1013, 1002 cm$^{-1}$; HRMS (EI+) calcd for C$_{13}$H$_9$O$_4$NS 275.02523, found 275.02455.

Example 7

O-Phenyl-O-3-pyridinyl thiocarbonate (8)

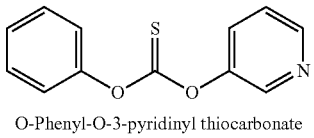 [SMILES: S=C(Oc1ccccc1)Oc1cccnc1]

O-Phenyl-O-3-pyridinyl thiocarbonate

Procedure B; white solid, mp 94-97° C.; 75%. $^1$H-NMR (400 MHz, CDCl3) δ 8.58 (1H, dd, J=1.2, 4.8 Hz), 8.56 (1H, d, J=2.6 Hz), 7.59 (1H, ddd, J=1.4, 2.8, 8.3 Hz), 7.48 (2H, m), 7.42 (1H, ddd, J=0.3, 4.8, 8.3 Hz), 7.35 (1H, m), 7.23 (2H, m); $^{13}$C-NMR (100 MHz, CDCl$_3$) δ 194.4, 153.6, 150.3, 147.9, 144.0, 130.0, 129.9, 127.2, 124.2 121.8; IR (KBr) 3053, 1875, 1590, 1492, 1478, 1457, 1428, 1371, 1321, 1310, 1282, 1267, 1249, 1193, 1160, 1097, 1071, 1038, 1023, 1002 cm$^{-1}$; HRMS (EI+) calcd for C$_{12}$H$_9$O$_2$NS 232.04322 [M+H]$^+$, found 232.04126 [M+H]$^+$.

Example 8

O-Ethyl-O-phenyl thiocarbonate (9)

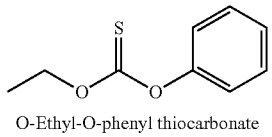

O-Ethyl-O-phenyl thiocarbonate

Procedure A; colorless oil, 89%. $^1$H-NMR (400 MHz, CDCl$_3$) δ 7.42 (2H, t, J=7.6 Hz), 7.29 (1H, t, J=7.3 Hz), 7.11 (2H, d, J=7.7 Hz), 4.60 (2H, q, J=7.1 Hz), 1.47 (3H, t, J=7.1 Hz); $^{13}$C-NMR (100 MHz, CDCl$_3$) δ; IR (KBr) 3058, 3043, 2984, 2937, 2904, 2870, 2491, 2410, 1942, 1864, 1762, 1733, 1675, 1593, 1490, 1464, 1457, 1398, 1372, 1282, 1191, 1155, 1095, 1061, 1044, 1023, 1004 cm$^{-1}$; HRMS (EI+) calcd for C$_9$H$_{10}$O$_2$S 182.04015, found 182.03956.

Example 9

O-[3-(4-Methoxyphenyl)propyl]-O-phenyl thiocarbonate (10)

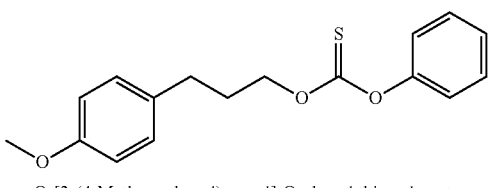

O-[3-(4-Methoxyphenyl)propyl]-O-phenyl thiocarbonate

Procedure A; colorless oil, 58%. $^1$H-NMR (400 MHz, CDCl$_3$) δ 7.43 (2H, t, J=7.5 Hz), 7.30 (1H, t, J=7.4 Hz), 7.13 (4H, m), 6.86 (2H, d, J=8.6 Hz), 4.54 (2H, t, J=6.4 Hz), 3.80 (3H, s), 2.73 (2H, t, J=7.3 Hz), 2.12 (2H, m); $^{13}$C-NMR (100 MHz, CDCl$_3$) δ 195.2, 158.0, 153.4, 132.8, 129.5, 129.3, 126.5, 121.9 113.9, 73.6, 55.3, 31.1, 30.0; IR (KBr) 3060, 3031, 2996, 2953, 2834, 2488, 1881, 1781, 1612, 1590, 1513, 1490, 1456, 1389, 1359, 1291, 1246, 1201, 1112, 1070, 1037, 1021, 1004 cm$^{-1}$; HRMS (EI+) calcd for C$_{17}$H$_{18}$O$_3$S 302.09767, found 302.09717.

Example 10

O-(1-Naphthyl)-O-phenyl thiocarbonate (11)

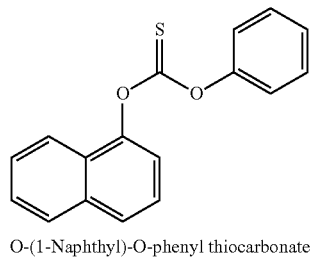 [SMILES: S=C(Oc1ccccc1)Oc1cccc2ccccc12]

O-(1-Naphthyl)-O-phenyl thiocarbonate

Procedure A; white solid, mp 59-61° C.; $^1$H-NMR (400 MHz, CDCl$_3$) δ 8.03 (1H, d, J=8.2 Hz), 7.94 (1H, d, J=7.7 Hz), 7.85 (1H, d, J=8.2 Hz), 7.6-7.5 (5H, m Hz), 7.41 (1H, d, J=7.5 Hz), 7.36 (1H, t, J=7.4 Hz), 7.31 (2H, d, J=7.9 Hz); $^{13}$C-NMR (100 MHz, CDCl$_3$) δ 194.7, 153.8, 149.5, 134.9, 129.9, 128.4, 127.2, 127.1, 127.0, 126.9, 126.5, 122.0, 121.3, 118.8; IF (KBr) IR (KBr) 3062, 2921, 2850, 2459, 1936, 1600, 1591, 1509, 1490, 1457, 1392, 1277, 1194, 1153, 1079, 1042, 1014, 1003, 921, 860, 844, 799, 770, 737, 688, 658, 604, 555, 482, 433, 410 cm$^{-1}$; HRMS (EI+) calcd for C$_{17}$H$_{12}$O$_2$S 280.05580, found 280.05450.

Example 11

O-(2-Naphthyl)-O-phenyl thiocarbonate (12)

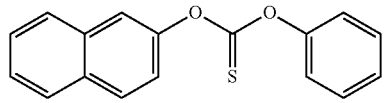

O-(2-Naphthyl)-O-phenyl thiocarbonate

Procedure A; white solid, mp 134-136° C.; 84%; $^1$H-NMR (400 MHz, CDCl$_3$) δ 7.91 (1H, d, J=8.92 Hz), 7.86 (2H, m), 7.66 (1H, d, J=2.28 Hz), 7.48 (4H, m), 7.37 (1H, dd, J=2.36, 8.88 Hz), 7.32 (1H, m), 7.26 (2H, m); $^{13}$C-NMR (100 MHz, CDCl$_3$) δ 194.89, 153.58, 151.04, 133.66, 131.85, 129.68, 127.92, 127.86, 126.84, 126.82, 126.26, 121.82, 121.02, 118.95; HRMS (EI+) calcd for C$_{17}$H$_{12}$O$_2$S 280.05580, found 280.05526.

Example 12

O-(6-Quinolinyl)-O-phenyl thiocarbonate (13)

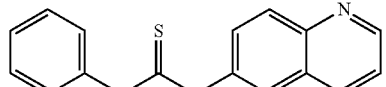

O-(6-Quinolinyl)-O-phenyl thiocarbonate

Procedure C; white solid, mp 139-141° C.; 54% $^1$H-NMR (400 MHz, CDCl$_3$) δ 8.94 (1H, dd, J=1.6, 4.2 Hz), 8.19 (2H, m), 7.66 (1H, d, J=2.56 Hz), 7.62 (1H, dd, J=2.64, 9.08 Hz), 7.45 (3H, m), 7.33 (1H, m), 7.25 (2H, m); $^{13}$C-NMR (100 MHz, CDCl$_3$) δ 194.6, 153.5, 151.0, 150.6, 146.5, 136.0, 131.3, 129.7, 128.5, 126.9, 124.8, 121.8, 121.7, 118.9; HRMS (ESI+) calcd for C$_{16}$H$_{11}$O$_2$NS 282.05887 [M+H]$^+$, found 28205879 [M+H]$^+$.

Example 13

O-(1-Phenanthryl)-O-phenyl thiocarbonate (14)

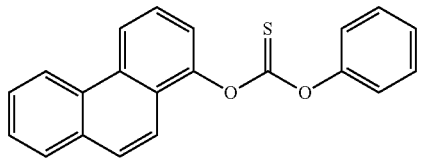

O-(1-Phenanthryl)-O-phenyl thiocarbonate

Procedure C; yellow solid, mp 96-98° C.; 79%; $^1$H-NMR (400 MHz, CDCl$_3$) δ 8.70 (1H, dd, J=1.92, 6.76 Hz), 8.65 (1H, d, J=8.04 Hz), 8.06 (1H, m), 7.88 (1H, d, J=7.68 Hz), 7.72-7.57 (4H, m), 7.44 (2H, m), 7.30 (3H, m), 7.21 (1H, m); $^{13}$C-NMR (100 MHz, CDCl$_3$) δ 194.4, 153.7, 147.8, 131.7, 131.3, 129.8, 129.7, 128.7, 127.5, 127.3, 127.2, 127.0, 126.9, 125.9, 123.2, 122.8, 121.9, 121.8, 118.5; HRMS (EI+) calcd for C$_{21}$H$_{14}$O$_2$S 330.07145, found 330.07140.

Example 14 p-Fluorophenyl Benzoate (15)

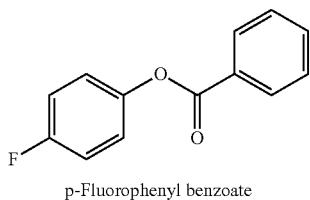 [SMILES: O=C(Oc1ccc(F)cc1)c1ccccc1]

p-Fluorophenyl benzoate (Synthesized from benzoyl chloride) White solid, mp 48-50° C.; 97%. $^1$H-NMR (400 MHz, CDCl$_3$) δ 8.20 (2H, d, J=7.1 Hz), 7.65 (1H, t, J=7.4 Hz), 7.52 (2H, t, J=7.8 Hz), 7.15 (2H, m), 7.12 (2H, t, J=8.1 Hz); $^{13}$C-NMR (100 MHz, CDCl$_3$) δ 165.1, 160.2 (d, J=242.7 Hz), 146.7, 133.6, 130.1, 129.2, 128.5, 123.0 (d, J=8.5 Hz), 116.1 (d, J=23.3 Hz); IR (KBr) 3454, 3065, 2926, 2854, 1886, 1733, 1599, 1584, 1504, 1450, 1416, 1316, 1266, 1186, 1088, 1064, 1024, 1013 cm$^{-1}$; HRMS (EI+) calcd for C$_{13}$H$_9$O$_2$F 216.05866, found 216.05698.

Example 15

Phenyl-p-phenylbenzoate (16)

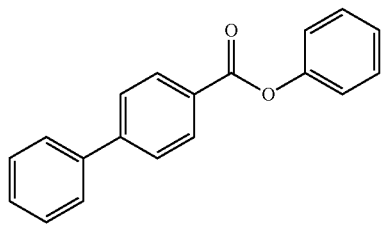

Phenyl-p-phenylbenzoate

White solid, mp 146-149° C.; 29%. $^1$H-NMR (400 MHz, CDCl3) δ; $^{13}$C-NMR (100 MHz, CDCl$_3$) δ; 8.27 (2H, d, J=8.4 Hz), 7.74 (2H, d, J=8.4 Hz), 7.66 (2H, d, J=7.2 Hz), 7.49 (2H, m), 7.42 (2H, m), 7.29 (2H, d, J=7.4 Hz), 7.24 (2H, m); $^{13}$C-NMR (100 MHz, CDCl$_3$) δ 165.0, 151.0, 146.3, 139.8, 130.7, 129.5, 128.9, 128.3, 128.2, 127.3, 127.2, 125.8, 121.7; IR (KBr) 2919, 1730, 1456, 1404, 1264, 1196, 1083 cm$^{-1}$; HRMS (EI+) calcd for C$_{19}$H$_{14}$O$_2$ 274.09938, found 274.09877.

Example 16

Phenyl Quinoline-6-Carboxylate (17)

6-Quinolinyl Benzoate

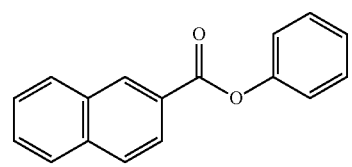

phenyl quinoline-6-carboxylate (Synthesized from benzoyl chloride) White solid, mp 77-79° C.; 69%; $^1$H-NMR (400 MHz, CDCl$_3$) δ 8.92 (1H, d, J=2.92 Hz), 8.24 (2H, d, J=7.12 Hz), 8.18 (1H, d, J=9.12 Hz), 8.14 (1H, dd, J=0.96, 8.36 Hz), 7.70 (1H, d, J=2.52 Hz), 7.66 (1H, m), 7.59 (1H, dd, J=2.56, 9.08 Hz), 7.53 (2H, m), 7.42 (1H, dd, J=4.24, 8.32 Hz); $^{13}$C-NMR (100 MHz, CDCl$_3$) δ 165.16, 150.26, 148.78, 146.33, 135.86, 133.87, 131.08, 130.25, 129.23, 128.69, 128.61, 124.88, 121.63, 118.62.

Example 17

Phenyl-9-phenanthroate (18)

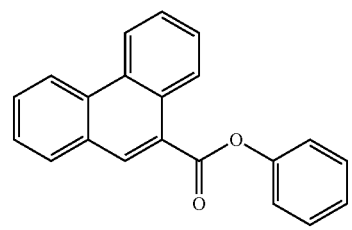

O-Phenyl-9-phenanthroate

White solid, mp 105-107° C.; 65%; $^1$H-NMR (400 MHz, CDCl$_3$) δ 9.07 (1H, m), 8.76 (3H, m), 8.04 (1H, d, J=7.72 Hz), 7.80 (1H, m), 7.72 (3H, m), 7.50 (2H, m), 7.33 (3H, m); $^{13}$C-NMR (100 MHz, CDCl$_3$) δ 165.8, 151.0, 133.6, 132.5 130.7, 130.2, 129.9, 129.5, 129.3, 129.1, 127.6, 127.1, 127.0, 126.5, 125.9, 124.9, 122.8, 122.7, 121.9; HRMS (EI+) calcd for C$_{21}$H$_{14}$O$_2$ 298.09938, found 298.09928.

Example 18

O-(4-Methoxyphenyl)-N-methyl-N-phenyl thiocarbamate (20)

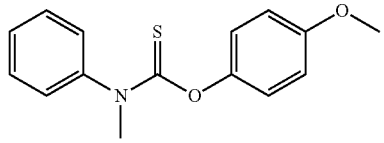

O-(4-Methoxyphenyl)-N-methyl-N-phenyl thiocarbamate

Procedure D, white solid, mp 109-111° C., 91%; $^1$H-NMR (400 MHz, CDCl$_3$) δ 7.44 (2H, m), 7.33 (3H, m), 6.90 (4H, m), 3.78 (3H, s), 3.74 (3H, s); $^{13}$C-NMR (100 MHz, CDCl$_3$) δ 188.5, 157.3, 147.6, 143.5, 129.4, 127.7, 125.6, 123.2, 114.1, 55.5, 44.8; IR (KBr) 3059, 3003, 2930, 2835, 1596, 1505, 1495, 1477, 1380, 1295, 1277, 1250, 1207, 1171, 1121, 1103, 1073, 1033, 1007 cm$^{-1}$; HRMS (EI+) calcd for C$_{15}$H$_{15}$O$_2$NS 273.08235, found 27308181.

Example 19

O-(4-Cyanophenyl)-N-methyl-N-phenyl thiocarbamate (21)

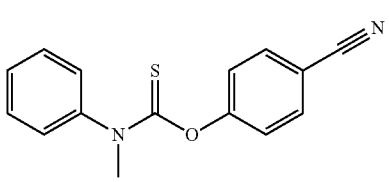

O-(4-Cyanophenyl)-N-methyl-N-phenyl thiocarbamate

Procedure D, white solid, mp 93-95° C., 93%; $^1$H-NMR (400 MHz, CDCl$_3$) δ 7.63 (2H, d, J=8.5 Hz), 7.45 (2H, t, J=7.4 Hz), 7.33 (3H, m), 7.12 (2H, d, J=8.6 Hz), 3.73 (3H, s); $^{13}$C-NMR (100 MHz, CDCl$_3$) δ 186.4, 157.0, 143.1, 133.3, 129.6, 128.1, 125.4, 123.9, 118.3, 109.7, 44.9; IR (KBr) 3099, 3062, 2930, 2854, 2228, 1953, 1903, 1776, 1731, 1669, 1599, 1479, 1384, 1292, 1218, 1159, 1122, 1085, 1017, 1024, 1003 cm$^{-1}$; HRMS (EI+) calcd for C$_{15}$H$_{12}$ON$_2$S 268.06704, found 268.06694.

Example 20

O-(4-Methylphenyl)-N-methyl-N-phenyl thiocarbamate (22)

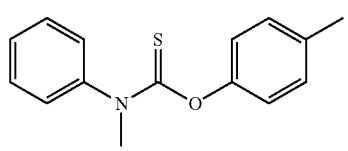

O-(4-Methylphenyl)-N-methyl-N-phenyl thiocarbamate

Procedure D, white solid, mp 75-77° C., 90%; $^1$H-NMR (400 MHz, CDCl$_3$) δ 7.44 (2H, m), 7.33 (3H, t, J=6.4 Hz), 7.15 (2H, d, J=7.6 Hz), 6.94 (2H, d, 7.6 Hz), 3.74 (3H, s), 2.33 (3H, s); $^{13}$C-NMR (100 MHz, CDCl$_3$) δ 188.3, 151.8, 143.5, 135.5, 129.7, 129.4, 127.6, 125.6, 122.1, 44.7, 20.9; IR (KBr) 3061, 3034, 2923, 1884, 1749, 1595, 1506, 1500, 1477, 1448, 1379, 1291, 1276, 1217, 1180, 1121, 1089, 1073, 1018, 1003 cm$^{-1}$; HRMS (ESI+) calcd for C$_{15}$H$_{15}$ONS 280.07720 [M+Na]$^+$, found 280.07765 [M+Na]$^+$.

Example 21

O-(3-Methylphenyl)-N-methyl-N-phenyl thiocarbamate (23)

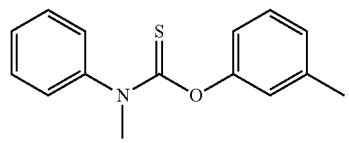

O-(3-Methylphenyl)-N-methyl-N-phenyl thiocarbamate

Procedure D, white solid, mp 82-84° C., 87%; $^1$H-NMR (400 MHz, CDCl$_3$) δ 7.44 (2H, m), 7.33 (3H, m), 7.24 (2H, m), 7.04-6.83 (3H, m), 3.75 (3H, s), 2.34 (3H, s); $^{13}$C-NMR (100 MHz, CDCl$_3$) δ 187.9, 153.9, 143.4, 139.2, 129.3, 128.7, 127.5, 126.6, 125.5, 122.9, 119.4, 44.6, 21.2; IR (KBr) 3037, 2919, 1587, 1493, 1478, 1379, 1243, 1157, 1119, 1002 cm$^{-1}$; HRMS (EI+) calcd for C$_{15}$H$_{15}$ONS 280.07720 [M+Na]$^+$, found 280.07971 [M+Na]$^+$.

Example 22

O-(4-Chlorophenyl)-N-methyl-N-phenyl thiocarbamate (24)

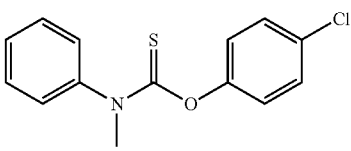

O-(4-Chlorophenyl)-N-methyl-N-phenyl thiocarbamate

Procedure D, white solid, mp 105-107° C., 97%; $^1$H-NMR (400 MHz, CDCl$_3$) δ 7.46 (2H, t, J=7.4 Hz), 7.35 (5H, m), 6.95 (2H, d, J=8.5 Hz), 3.73 (3H, s); $^{13}$C-NMR (100 MHz, CDCl$_3$) δ 187.5, 152.4, 143.3, 131.3, 129.5, 129.2, 127.8, 125.5, 123.9, 44.8; IR (KBr) 3090, 3074, 3061, 2976, 2932, 2771, 2561, 2422, 2334, 2258, 2172, 2087, 2015, 1976, 1949, 1909, 1885, 1870, 1819, 1791, 1739, 1676, 1645, 1595, 1485, 1453, 1429, 1391, 1313, 1284, 1214, 1162, 1128, 1086, 1072, 1029, 1015, 1002 cm$^{-1}$; HRMS (ESI+) calcd for C$_{14}$H$_{12}$ONSCl 300.02258 [M+Na]$^+$, found 300.02547 [M+Na]$^+$.

Example 23

O-(4-Methoxycarbonylphenyl)-N-methyl-N-phenyl thiocarbamate (25)

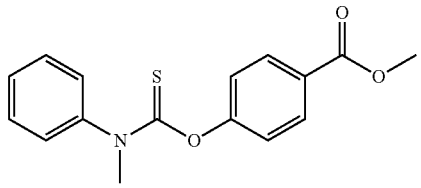

O-(4-Methoxycarbonylphenyl)-N-methyl-N-phenyl thiocarbamate

Procedure E, white solid, mp 108-110° C., 71%; $^1$H-NMR (400 MHz, CDCl$_3$) δ8.03 (2H, d, J=8.4 Hz), 7.44 (2H, m), 7.33 (3H, m), 7.07 (2H, d, J=8.48 Hz), 3.89 (3H, s), 3.73 (3H, s); $^{13}$C-NMR (100 MHz, CDCl$_3$) δ 186.9, 166.1, 157.3, 143.2, 130.7, 129.4, 127.7, 127.6, 125.4, 122.6, 52.0, 44.7; IR (KBr) IR (KBr) 2925, 1723, 1599, 1495, 1386, 1277, 1175, 1109, 1010 cm$^{-1}$; HRMS (EI+) calcd for C$_{16}$H$_{15}$O$_3$NS 324.06703 [M+Na]$^+$, found 324.06975 [M+Na]$^+$.

Example 24

O-(4-Phenylphenyl)-N-methyl-N-phenyl thiocarbamate (26)

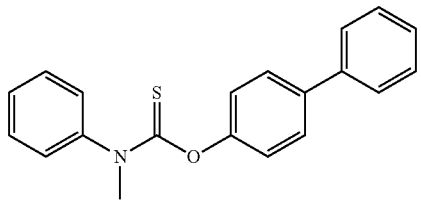

O-(4-Phenylphenyl)-N-methyl-N-phenyl thiocarbamate

Procedure E, white solid, mp 128-130° C., 82%; $^1$H-NMR (400 MHz, CDCl$_3$) δ 7.57 (4H, m), 7.44 (4H, m), 7.35 (4H, m), 7.10 (2H, d, J=8.08 Hz), 3.77 (3H, s); $^{13}$C-NMR (100 MHz, CDCl$_3$) δ 187.8, 153.3, 143.4, 140.2, 138.9, 129.3, 128.6, 127.8, 127.6, 127.2, 127.0, 125.5, 122.6, 44.7; IR (KBr) 2920, 1595, 1595, 1381, 1225, 1180, 1118, 1006 cm$^{-1}$; HRMS (EI+) calcd for C$_{20}$H$_{17}$ONS 342.09285 [M+Na]$^+$, found 342.09564 [M+Na]$^+$.

Example 25

O-(1-Naphthyl)-N-methyl-N-phenyl thiocarbamate (27)

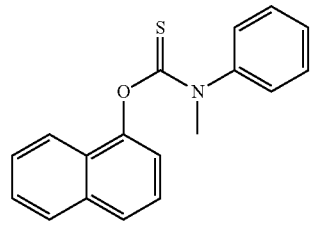

O-(1-Naphthyl)-N-methyl-N-phenyl thiocarbamate

Procedure D, white solid, mp 99-101° C., 78%; $^1$H-NMR (400 MHz, CDCl$_3$) δ 7.85 (1H, m), 7.71 (2H, m), 7.47 (7H, m), 7.36 (1H, m), 7.19 (1H, d, J=7.4), 3.81 (3H, s); $^{13}$C-NMR (100 MHz, CDCl$_3$) δ 186.9, 148.9, 142.6, 133.5, 128.5, 127.0, 126.8, 126.3, 125.3, 125.2, 125.0, 124.6, 124.1, 120.4, 118.2, 43.8; IR (Kbr) 3059, 2929, 1597, 1493, 1477, 1448, 1379, 1291, 1276, 1256, 1227, 1180, 1166, 1153, 1125, 1073, 1024, 1012 cm$^{-1}$; HRMS (ESI+) calcd for C$_{18}$H$_{15}$ONS 316.07720 [M+Na]$^+$, found 316.07901 [M+Na]$^+$.

Example 26

O-(2-Naphthyl)-N-methyl-N-phenyl thiocarbamate (28)

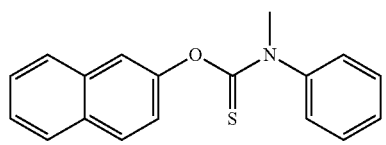

O-(2-Naphthyl)-N-methyl-N-phenyl thiocarbamate

Procedure D, white solid, mp 129-131° C.; 88%; $^1$H-NMR (400 MHz, CDCl$_3$) δ 7.78 (3H, m), 7.41 (5H, m), 7.31 (3H, m), 7.19 (1H, m), 3.74 (3H, s); $^{13}$C-NMR (100 MHz, CDCl$_3$) δ 188.06, 151.63, 143.58, 133.68, 131.55, 129.53, 129.04, 127.90, 127.81, 127.74, 126.54, 125.79, 125.71, 122.26, 119.35; HRMS (ESI+) calcd for C$_{18}$H$_{15}$ONS 294.09526 [M+H]$^+$, found 294.09548 [M+H]$^+$.

Example 27

O-(6-Quinolinyl)-N-methyl-N-phenyl thiocarbamate (29)

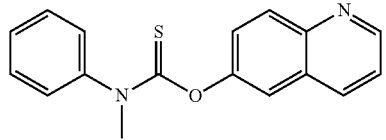

O-(6-Quinolinyl)-N-methyl-N-phenyl thiocarbamate

Procedure F, white solid, mp 124-126° C.; 35%; $^1$H-NMR (400 MHz, CDCl$_3$) δ 8.88 (1H, m), 8.09 (2H, m), 7.42 (7H, m), 3.77 (3H, s); $^{13}$C-NMR (100 MHz, CDCl$_3$) δ 187.6, 151.7, 150.2, 146.4, 143.4, 135.8, 130.6, 129.5, 128.4, 127.9, 125.9, 125.6, 121.5, 119.2, 44.9; HRMS (ESI+) calcd for C$_{17}$H$_{14}$ON$_2$S 295.09051 [M+H]$^+$, found 295.09110 [M+H]$^+$.

Example 28

O-Phenyl-N,N-diethyl thiocarbamate

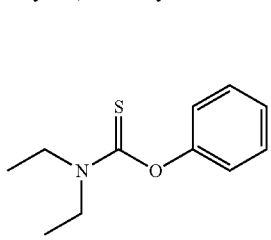

O-Phenyl-N,N-diethyl thiocarbamate

Procedure D was followed with the only exception that for Et$_3$N (dealkylating procedure of D. S. Millan, R. H. Prager, *Aust. J. Chem.* 1999, 52, 841.) has been used instead of N-methyl aniline.

Example 29

4-Methoxy-N-methyl-N-phenyl benzamide (30)

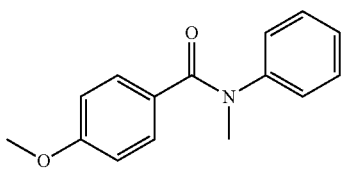

4-Methoxy-N-methyl-N-phenyl benzamide

Colorless Yellow oil, 80%; $^1$H-NMR (400 MHz, CDCl$_3$) δ 7.25 (4H, m), 7.14 (1H, t, J=7.3 Hz), 7.04 (2H, d, J=7.7 Hz), 6.66 (2H, d, J=8.7 Hz), 3.74 (3H, s), 3.48 (3H, s); $^{13}$C-NMR (100 MHz, CDCl$_3$) δ HRMS (EI+) calculated for C$_{15}$H$_{15}$O$_2$N 241.11028, found 241.11020.

Example 30

4-Methyl-N-methyl-N-phenyl benzamide (31)

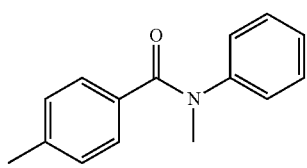

4-Methyl-N-methyl-N-phenyl benzamide

Colorless Yellow oil, 72%; $^1$H-NMR (400 MHz, CDCl$_3$) δ 7.20 (4H, m), 7.13 (1H, tt, J=1.2, 6.6 Hz), 7.03 (2H, d, J=7.2 Hz), 6.95 (2H, d, J=7.8 Hz), 3.48 (3H, s), 2.24 (3H, s); $^{13}$C-NMR (100 MHz, CDCl$_3$) δ 170.7, 145.2, 139.8, 132.9, 129.1, 128.9, 128.3, 126.8, 126.3, 38.5, 21.3; IR (KBr) 2922, 1644, 1595, 1495, 1418, 1364, 1301, 1106, 1030 cm$^{-1}$; HRMS (EI+) calculated for C$_{15}$H$_{15}$ON 225.11537, found 225.11457.

Example 31

3-Methyl-N-methyl-N-phenyl benzamide (32)

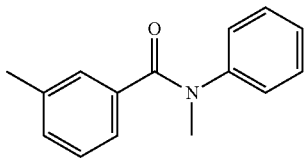

3-Methyl-N-methyl-N-phenyl benzamide

Colorless Yellow oil, 76%; $^1$H-NMR (400 MHz, CDCl$_3$) δ 7.24-7.18 (3H, m), 7.13 (1H, tt, J=1.2, 6.6 Hz), 7.03 (H, m), 6.99 (H, m), 3.48 (3H, s), 2.21 (3H, s); $^{13}$C-NMR (100 MHz, CDCl$_3$) δ 170.8, 144.9, 137.5, 135.8, 130.2, 129.4, 129.0, 127.4, 126.8, 126.3, 125.7, 38.3, 21.1; IR (KBr) 3039, 2921, 1646, 1585, 1495, 1363, 1302, 1158, 1106, 1032 cm$^{-1}$; HRMS (EI+) calculated for C$_{15}$H$_{15}$ON 225.11402, found 225.11475.

Example 32

4-Methoxycarbonyl-N-methyl-N-phenyl benzamide (33)

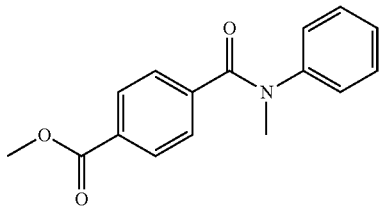

4-Methoxycarbonyl-N-methyl-N-phenyl benzamide

White solid, mp 78-80° C., 97%; $^1$H-NMR (400 MHz, CDCl$_3$) δ 7.83 (2H, d, J=8.4 Hz), 7.34 (2H, d, J=8.4 Hz), 7.21 (2H, m), 7.14 (1H, tt, J=1.2, 6.2 Hz), 7.01 (2H, d, J=7.4 Hz), 3.86 (3H, s), 3.50 (3H, s); $^{13}$C-NMR (100 MHz, CDCl$_3$) δ 169.6, 166.3, 144.2, 140.2, 130.7, 129.2, 129.0, 128.5, 126.9, 52.2, 38.2; IR (KBr)) 2952, 1723, 1645, 1595, 1496, 1436, 1370, 1278, 1178, 1108, 1020 cm$^{-1}$; HRMS (EI+) calculated for C$_{16}$H$_{15}$O$_3$N 269.10520, found 269.10487.

Example 33

4-Phenyl-N-methyl-N-phenyl benzamide (34)

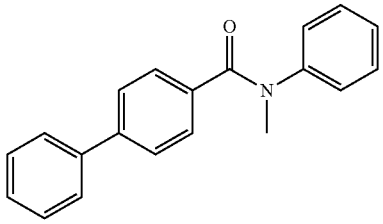

4-Phenyl-N-methyl-N-phenyl benzamide

White solid, mp 99-102° C., >99%; $^1$H-NMR (400 MHz, CDCl$_3$) δ 7.51 (2H, m), 7.36 (7H, m), 7.24 (2H, m), 7.15 (1H, m), 7.06 (2H, m), 3.52 (3H, s); $^{13}$C-NMR (100 MHz, CDCl$_3$) δ 170.3, 144.9, 142.2, 140.1, 134.6, 129.3, 129.2, 128.7, 127.7, 127.0, 126.9, 126.5, 126.3, 38.5; IR (KBr) 3031, 2923, 1644, 1595, 1495, 1419, 1364, 1301, 1281, 1106, 1008 cm$^{-1}$; HRMS (EI+) calculated for C$_{20}$H$_{17}$ON 287.13102, found 287.13032.

Example 34

N-Methyl-N-phenyl-2-naphthamide (35)

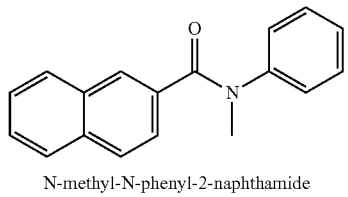 [SMILES: CN(C(=O)c1ccc2ccccc2c1)c1ccccc1]

N-methyl-N-phenyl-2-naphthamide

White solid, mp; 79%; $^1$H-NMR (400 MHz, CDCl$_3$) δ 7.89 (1H, s), 7.71 (2H, m), 7.58 (1H, d, J=8.56), 7.45 (2H, pd, J=1.4, 6.84 Hz), 7.31 (1H, dd, J=1.64, 8.56 Hz), 7.19 (2H, m), 7.09 (3H, m); $^{13}$C-NMR (100 MHz, CDCl$_3$) δ 187.66, 151.70, 150.25, 146.40, 143.45, 135.84, 130.61, 129.57, 128.43, 127.93, 125.93, 125.64, 121.52, 119.24, 44.90; HRMS (CI+) calculated for C$_{18}$H$_{16}$ON 262.12319, found 262.12351.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description and shown in the accompanying drawings shall be interpreted as illustrative and not in a limiting sense.

What is claimed is:

1. A method for the preparation of an aromatic carboxylic acid aryl ester, the method comprising:
   contacting an O,O-diaryl thiocarbonate with a reactant that regioselectively reacts with sulfur, which contact causes an O-neophyl rearrangement, thereby forming the aromatic carboxylic acid aryl ester.

2. The method of claim 1 wherein the reactant that regioselectively reacts with sulfur comprises a Si-centered radical.

3. The method of claim 2 wherein the Si-centered radical is formed by contacting a silane with a peroxide or a diazene.

4. The method of claim 1 wherein the reactant that regioselectively reacts with sulfur comprises a Sn-centered radical.

5. The method of claim 4 wherein the Sn-centered radical is formed by contacting a stannane with a peroxide or a diazene.

6. The method of claim 1 further comprising the step of contacting an aromatic alcohol with a compound comprising a thiocarbonyl moiety to thereby prepare the O,O-diaryl thiocarbonate.

7. The method of claim 6 wherein the O,O-diaryl thiocarbonate is a symmetric O,O-diaryl thiocarbonate.

8. The method of claim 6 wherein the O,O-diaryl thiocarbonate is an asymmetric O,O-diaryl thiocarbonate.

9. A process for the preparation of a benzoate having the Structure (I):

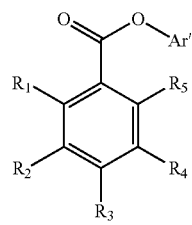

Structure (I)

wherein R$_1$, R$_2$, R$_3$, R$_4$, and R$_5$ are each independently a hydrogen, an alkyl, an alkenyl, an alkynyl, an alkoxy, a cyano, an aryl, an aromatic heterocycle, an ester, an amino, a hydrazide, an amide, thioether, sulfone, sulfoxide, sulfonic esters, and sulfinic esters, a carboxylate, or a halide; any R$_1$, R$_2$, R$_3$, R$_4$, and R$_5$ together with an adjacent R group and the atoms to which they are bonded may optionally form a cyclic moiety; and Ar' is a substituted or unsubstituted aromatic moiety; the process comprising:
   contacting an aromatic alcohol reactant with a thiocarbonyl compound reactant to thereby form an intermediate thiocarbonate product, wherein said aromatic alcohol reactant has the Structure (II):

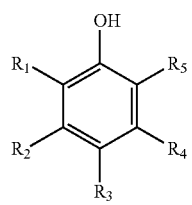

Structure (II)

wherein R$_1$ through R$_5$ are as defined above in connection with Structure (I); said thiocarbonyl compound has the Structure (III):

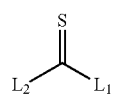

Structure (III)

wherein L$_1$ and L$_2$ are each leaving groups; and said thiocarbonate product has the Structure (IV):

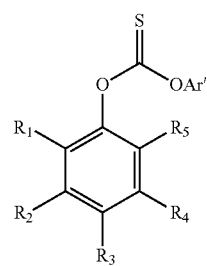

Structure (IV)

wherein R$_1$ through R$_5$ and Ar' are as defined above in connection with Structure (I); and
   contacting the intermediate thiocarbonate product having Structure (IV) with a reactant that regioselectively reacts with sulfur, which contact causes an O-neophyl rearrangement, thereby forming the benzoate having the Structure (I).

10. A method for the preparation of an N-aryl aromatic carboxamide, the method comprising:

contacting an O-aryl-N-aryl thiocarbamate with a reactant that regioselectively reacts with sulfur, which contact causes an O-neophyl rearrangement, thereby forming the N-aryl aromatic carboxamide.

11. The method of claim 10 wherein the reactant that regioselectively reacts with sulfur comprises a Si-centered radical.

12. The method of claim 11 wherein the Si-centered radical is formed by contacting a silane with a peroxide or a diazene.

13. The method of claim 10 wherein the reactant that regioselectively reacts with sulfur comprises a Sn-centered radical.

14. The method of claim 13 wherein the Sn-centered radical is formed by contacting a stannane with a peroxide or a diazene.

15. The method of claim 10 further comprising the steps of:

contacting an aromatic alcohol with a compound comprising a thiocarbonyl moiety to thereby prepare an O-aryl thiocarbonyl intermediate; and contacting the O-aryl thiocarbonyl intermediate with an aniline to thereby prepare the O-aryl-N-aryl thiocarbamate.

16. A process for the preparation of a benzamide having the Structure (V):

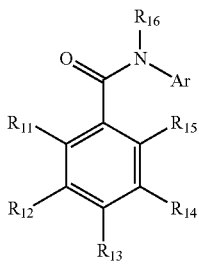

Structure (V)

wherein $R_{11}$, $R_{12}$, $R_{13}$, $R_{14}$, and $R_{15}$ are each independently a hydrogen, an alkyl, an alkenyl, an alkynyl, an alkoxy, a cyano, an aryl, an aromatic heterocycle, an ester, an amino, a hydrazide, an amide, thioether, sulfone, sulfoxide, sulfonic esters, and sulfinic esters, a carboxylate, or a halide; any $R_{11}$, $R_{12}$, $R_{13}$, $R_{14}$, and $R_{15}$ together with an adjacent R group and the atoms to which they are bonded may optionally form a cyclic moiety; $R_{16}$ is a hydrogen, a hydrocarbyl, or an aryl; and Ar is a substituted or unsubstituted aromatic moiety; the process comprising:

contacting an aromatic alcohol reactant with a thiocarbonyl compound reactant to thereby form an intermediate product, wherein said aromatic alcohol reactant has the Structure (VI):

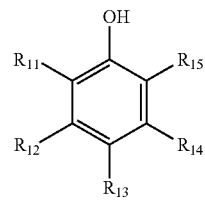

Structure (VI)

wherein $R_{11}$, $R_{12}$, $R_{13}$, $R_{14}$, and $R_{15}$ are as defined above in connection with Structure (V); said thiocarbonyl compound reactant has the Structure (VII):

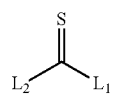

Structure (VII)

wherein $L_1$ and $L_2$ are each leaving groups, and said intermediate product has the Structure (VIII):

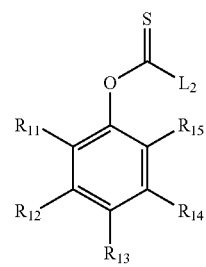

Structure (VIII)

wherein $R_{11}$, $R_{12}$, $R_{13}$, $R_{14}$, and $R_{15}$ are as defined above in connection with Structure (V) and $L_2$ is a leaving group;

contacting the intermediate product having the Structure (VIII) with an aniline to thereby form a thiocarbamate product, wherein said aniline has the Structure (IX):

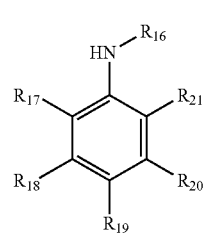

Structure (IX)

wherein $R_{16}$ is a hydrogen, a hydrocarbyl, or an aryl; $R_{17}$, $R_{18}$, $R_{19}$, $R_{20}$, and $R_{21}$ are each independently a hydrogen, an alkyl, an alkenyl, an alkynyl, an alkoxy, a cyano, an aryl, an aromatic heterocycle, an ester, an amino, a hydrazide, an amide, thioether, sulfone, sulfoxide, sulfonic esters, and sulfinic esters, a carboxylate, or a halide, and any $R_{17}$, $R_{18}$, $R_{19}$, $R_{20}$, and $R_{21}$ together with an adjacent R group and the atoms to which they are bonded may optionally form a cyclic moiety; and said thiocarbamate product has the Structure (X):

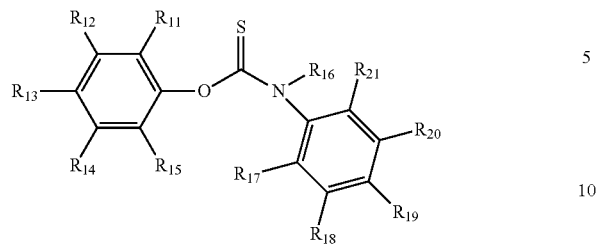

Structure (X)

wherein $R_{11}$ through $R_{16}$ are as defined above in connection with Structure (V); and $R_{17}$ through $R_{21}$ are as defined above in connection with Structure (IX); and contacting the thiocarbamate product having the Structure (X) with a reactant that regioselectively reacts with sulfur, which contact causes an O-neophyl rearrangement, thereby forming the benzamide having the Structure (V).

\* \* \* \* \*